United States Patent
Khatib et al.

(10) Patent No.: US 8,569,574 B2
(45) Date of Patent: Oct. 29, 2013

(54) METHODS AND COMPOSITIONS FOR IMPROVED FERTILIZATION AND EMBRYONIC SURVIVAL

(75) Inventors: Hasan Khatib, Madison, WI (US); Ricky L. Monson, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 651 days.

(21) Appl. No.: 12/267,076

(22) Filed: Nov. 7, 2008

(65) Prior Publication Data
US 2009/0253952 A1  Oct. 8, 2009

Related U.S. Application Data

(60) Provisional application No. 60/986,238, filed on Nov. 7, 2007.

(51) Int. Cl.
*A01K 67/00* (2006.01)
*A61D 19/00* (2006.01)
*C12Q 1/68* (2006.01)

(52) U.S. Cl.
USPC ............. 800/21; 800/15; 435/6.11; 435/6.12; 600/33; 600/34; 600/35; 506/13; 506/16

(58) Field of Classification Search
None
See application file for complete search history.

(56) References Cited

U.S. PATENT DOCUMENTS

2005/0123929 A1* 6/2005 Khatib .............................. 435/6
2007/0234437 A1* 10/2007 Khatib ............................ 800/14

OTHER PUBLICATIONS

Seyfert et al., J. Mol. Evol., 2000, 50:550-561.*
Kozcan et al., Nucleic Acids Research, 1991, 20:5591-5596.*

* cited by examiner

*Primary Examiner* — Christopher M Babic
*Assistant Examiner* — Jeremy C Flinders
(74) *Attorney, Agent, or Firm* — Kening Li; Pinsent Masons LLP

(57) ABSTRACT

Single nucleotide polymorphic sites at positions 3117, 12195, 13244, 13319, and 13516 of the bovine STAT5 gene are associated with improved fertilization rate and/or improved embryo survival rate. Also disclosed are nucleic acid molecules, kits, methods of genotyping and marker assisted bovine breeding methods.

22 Claims, 7 Drawing Sheets

Figure 1

```
   1 caggagcccc ggccgggagc gagcgccggc ccagtcgccg gaccgcccgg cacgaccagg
  61 tgggtggccc cggcagcgcg cccccggcga cgcgcgccca gaggggcac cctgctgctg
 121 ctgctgctgc tgctgccgcc gcccgggtcc tcgcccgca ggccccggag cccgacagac
 181 ggaggggcgc tggggacggt ccccgggacc cagggagagt ttcggcgccg cgtggactag
 241 ggacgcggga cgcggatgga gggaggaggc cgaggtgggg cgccgtcctc gccctcggtg
 301 ggcaggggc gctgtcggac tggatagtgg gagacgtcgg ggcacagcga ggtgcggggg
 361 gcgcagcccg agagagggag tgtcttgtct ccccagccct ccctcctaaa cacccagcc
 421 acgtgccagc ggtggccgag ccgtccaggg gaaaccttcg gtggccttgc cctagctttg
 481 ggctggaata tccccgcgtt cccagaaact gagactcggg gttcgaagca gggtaggggg
 541 tgtttgcagt cctccccaga gggcccgagg gcctccgcca tcaagtttct ctttcagttt
 601 ctagctgttc cccccacccc caccccggga agcccggtg gggcgagggg agaggaagaa
 661 ggggagggca cctgactttc gggagcccct cccaagcct cagcgggttc ctcgctggag
 721 ggaaggacgg ccttcccctc ctcaccgtct ttcttcccgc acaggaaagc gtgtctgtgg
 781 gaggggaggg gcctggcctg accgcggtcc agggatgggt gggcacggca gggccagggg
 841 caggcccagt ccacgcctgt gacgagaagg cacctcctca gcgctctgct cgccctaggt
 901 gaacggacat ggcgggctgg atccaggccc agcagctgca gggagatgcc ctgcgccaga
 961 tgcaggtgct atacgggcag cacttcccca tcgaggtccg gcattacttg gcacagtgga
1021 ttgagagcca gccgtggtag gtgcccctgc ccggcgcctt gccctgctgg tgctaacca
1081 tcaaggcccc ttggcctta cgtctcctct tggtggtttg gggagattct gatcctggct
1141 gtccctcact gtgtggaagg ggtggtgtcc cagggaaagg ggaacaggga aatgggagtc
1201 tgggagggga gagggatgt ttctagactc tgatggctgt ggagctgcag ggagcaagtc
1261 ttgtgggcag gagcctggga ttttcccgtc cttcctggta cctgacctcc tcatccgagg
1321 aggcaccata gcaggtttct ctctcctgcc ttgcgctaag ggatgccatc gacctggaca
1381 atccccagga ccgggcccag gccacccagc tcctggaggg cctggtgcag gagttgcaga
1441 agaaggcaga gcaccaagtc ggggaagacg ggttccttct gaagatcaag ctggggcact
1501 atgccacgca gctccaggtg ggcgtgagct gcaagccgtc tgcagggaaa cggtgtcggc
1561 cttctctttc cagcaccaga accctgggt ttttcctgg tttggccact gactcactgt
1621 atgaccctga gcttatctgt gcttcaattt ccccacccc ctctttctaa atcagacctg
1681 tcagattccc ttagcctatg acaaagtaag agacgggca tgtttgtccc caagagaagg
1741 gggatgggtg aaagcacttt ctgggtagat caggcagaag ggatgggagt agcctgagtc
1801 aaaattctgt tgttgagaga aacgaacacc gacagattct agaaaggagg ggatgggcaa
1861 ccagacagct ctcttggggc aagtggcgag cgagaggagc agcgttgtcc tggagccttg
1921 aattaagggt ttaatgtaag gtgagggtgt gggaggaagg agtaaagggg aaagaggaaa
1981 tttttgtgga aataggaaag ggatgtggat ggtaatcata gatgagcatt tattggaact
2041 cacttgaagt tttagagagc cttcttgaat acaagcagca gggtgccaag gaaataaaaa
2101 gtccatccca aaggaggcag gaaacagaag aaacctgggc tgtgggggt gtgggaaggg
2161 aagtaaaata ggaacccagg gccaggacta taatggaaag taccttgacc ttggcattag
2221 atgccccgag tcttgagtca tctgctcact cacttgtttg cctttggaca agtactcaat
2281 ctctctgagc atcagtattc tcatctgtga aatgaggata atggtttctg cttgtgttat
2341 agggtttcta tgatgcacaa gtcaaaggag atggcagatt ggaagtactt tgtaacctgt
2401 ggctttctaa tgcagtgtga accgaatgtg aagatctggg aggggaaatc aagtcaagga
2461 gagatagagg ttctggtggc agttcctgag gcttccgagt ggaagctgag gcataggctg
2521 gaggagagga aggagtgggg ggcactgcag tgggcatggt gggagcagag ggtggccttt
2581 ggtagccact gttggattct ttcagaacac gtacgaccgc tgccccatgg agctggtgcg
2641 ctgcattcgc cacattctgt acaatgaaca gaggctggtc cgagaagcca caatgtgag
2701 tgtccatgg gtttgggaa agattttgag aagtccttc acctgctctc ctctccagac
2761 acagctctgt tttataaata ctggcaagag agagcaccaa agaaataaaa cacacaggca
2821 agtgtgagag gccatattac atgcaggttt agattgaccc cacacacaca cagagccccc
2881 actccctggc tctatttact agctgtgcga cttgagcaag ttacttcacc tctctgagcc
2941 tccgattttt tcctattata aatgagggca gtcacagtat ctactctata gggctatttc
3001 gaggattaaa tgagatacca tgtgggcaaa ggatgtgtgc tgtgtgttta atcgttcagt
3061 cgtgtctgac tctctgcagc cctggggact gtagcctgcc aagctcctct gtctgtagaa
```

Figure 1 (Continued)

```
3121 ttttccaggc aagaatactg gagcaggttg ccatttcta ctccagggga tcttcccgac
3181 ccagagatca aacccacatc tcttgtgtcc cctgccttgg caggtggatt ctttaccact
3241 gagccacctg ggaagcccag agcaaagaac agacatatac aaatgaagaa gaggaagccc
3301 taaaaacata tgcacatctg gaaactcaat ctatgtcaga gatggcatta caaatcacta
3361 gggaaaagat ttgtcattga ataaatgagg ccggggcaaa agaagaaata tcctctggcg
3421 gggtctatga ggagaaatgg aggtctgtgt cagaagaatt aacctgggca agctcagaga
3481 agcaaggccc agggaggcag agcagggacc tattccccag gttctgaaat cataaagatc
3541 tcggacatat gcttcgacag tggtgcaaat ggtacattat ccacagtaaa gcaaaatgaa
3601 tttcattaaa tgatatccct taggtaatga ccacagaata atgcctgaag tgaagtcata
3661 gttattattt acttgtggtg gacactgata tcaagaattt gagaggtcat tcagtaaaca
3721 tttatcgagg tcctgctgtg cgtctgacac tggactagga tgggagaaac agataaagtc
3781 ctggcttcca cctaaaaggg atttgggctg tgatagattc tttaggactc tgctgagtgc
3841 taagtcagcc tatatggaaa aaggacccaa ctcagattgg ggcaggctgg ccagtagtgg
3901 ggagggtgtc cagaggaaaa agatgcctga ctgtaatgag gaaacaggga ggaagaaggt
3961 ggaatgagtt ttctagtgaa aaatagcagc agtaggattt ccctggtggt ccagtggtta
4021 aggccccacc ttccactgca ggaggcatgg gtttgatccc tggttgggga attaagatac
4081 cacataccac aaggtgcagc caaaaataga aataaagaaa atgcaaaata aataaatagc
4141 aacagtatat atgagggcag gaaggcacaa gccatcttat gacatttgaa gaattttaag
4201 tgtttagtga tcctgggaag aagggagccg actgggcaga agccaggtca cagagggtta
4261 actggtacaa ttcttgactt ggtgcaatta cagagctatc tgtaaacgta ggaatgagtc
4321 cagttccagt taagaaatac ctgcctacaa ggcaggtgct gttatgtttg gggaaaaat
4381 agtcctccag tcatcaagct gttcttggac acctctgacg ttctgggcct tgaagatttt
4441 gttgtgcacc aaatgggaca aagtcttggt ccttagggag ctcactttct agtgcagaga
4501 ggcagacaag aaagaacatg caggaacatg acacgttcag tagggcagtc ctattttaat
4561 gtaactcttc agaagaggtc actctgaaaa ggtgccagtg gaagtgccag cctcaggagg
4621 atttagtgcc agaatgttcc agggtaatgg aacaaaacat gcaaacgccc tgaggcagga
4681 actccctgcg tatccaagga acagaaagtg gccagtgtgg tttagcaaca agggagctgg
4741 gggtgcaggg ggcagaggct cctggctagg gccgtggagg ctgtgaaggg agtttgggtt
4801 ttattctgag agcagtttac tggagaggcc ctaaaaattt ggttgaggac tgccctggga
4861 gcccagtgct taagaatctg cctgcccatg gcggggacat gggttcaatt cctggtgccg
4921 gaagattcca aatgccatgg tgcacctaag cccatgggac acaactactg agctctagag
4981 cctgtgctct gcaacaagag aagccactgc aatgagcacc acagctagag agtagccagc
5041 ccatgagcag taacaaagac ccagcacagc ccaaaataag taagtaaaat aaaaacaaga
5101 acagcacttg gttgaaggaa tagatccaac cggattagct gaatggctgg atccacaaag
5161 cctttgttga tgcctccttg taccttcatt tggggtctt caggactcca cccacgagca
5221 gttcacactc ttccctcagt cctgaggtct tagtgaggac acagaacgta tgttcacatg
5281 gctttgttcc ccatcatgtc cccagcatct agcatcatgg catggggtca gtgaatgact
5341 gaaatgaggg gccatcatcc ttagtaggaa aactcaggta actcctggga tgggttgggt
5401 tctagtctct ccagagagaa ctcaaatgga ccttgtgtgg ggtactcaga tggaggtcag
5461 aactgcaaca gaagtttcta ccagtctctg ccaggtcacc tatttctcgt cctttacccc
5521 ctacacccct attttgccaa atgactcttc ttctgactca aagtacccct ccttcttatt
5581 ctagatttgg tgtctgcggt ctgtagtatt ggtgttcccc aaggcctgag gttttctcc
5641 catcctcact gcccagctca ctgctgcctg cacctcccc tgatatgtct ccagggtagt
5701 tcttctgctg ggatcctggt tgatgccatg tcccagaaac accttcagat caaccagaca
5761 tttgaggaac tgcgactggt cacgcaggac acagagaatg agctgaagaa gctgcagcag
5821 actcaagagt atttcatcat ccagtatcag gagagcctga ggatccaggg tgagcctggt
5881 gtgggagggc agtgcatgtc tggaggacca gagtgagacc actttgtgaa ctcctgcagg
5941 gttggggctg ggtccatgtc tgtctcccca gagccttacc caaagcttgg gacaagtaac
6001 ggctccagtg atggagcccc tgctgtgggc caggctccag gctaaaccct tattcaatac
6061 aaccttact caatacgact gtgttattca acacaacttt taccatagcc ctaagaatta
6121 agtgggggttt ccctggtggc tcagatagta aagaatctgc ctgcaatgca ggagacccag
6181 gttcggttcc tggtcagga agattccctg gagaagggaa tggctcccca cttcagtatt
6241 ctttattcct gttttgcaaa taataaaact gatgttcaaa gagaacatgc aatttggcct
6301 gggcttcttg taagttgcag aactggatgt taactagaga tattcataaa atccttatat
6361 tttattaacc agtattttgt atctcggtga aagaatgaat gaatgtggac agtgttcccc
6421 aatcagaggg aaaacctagg ttgggagtcc cctggttgaa ccaggctggg gagaggtgga
6481 acccccaggaa tgcccttct tgagcttcac taataggagg taaagatggg aggaggacgc
6541 gacagtggaa aactctgctg tctcccaggt ctataatttt ctagtagctg ccatgattag
```

Figure 1 (Continued)

```
 6601 ggtgtggggg aaaaattaac ccagaaggaa ttaaccccac taagtgtcct tacggtacac
 6661 tttgaagagc cttgaaacat gactcatctt cctccacttc aaattgaccc cagagctgta
 6721 tcaccccat ctaagtgaga acaggaagcc acctttcct tgttcttatt tttctgactt
 6781 cttaaggtag aacctcaggt cattgatttt agacccttct tttttctaat gtatatattc
 6841 agagctactg atttccctct cattaatgct tcagctgcat ctcatcatct tggatatgct
 6901 gtataccatt atcattcaat ttgaaatatt ttctaatttc tcttctgttt attttaccca
 6961 tacactattt agacgtatat tgtttaattt ccaaatattt gagtttttc tagatgtcat
 7021 accattattg atttcatttt gtggctgagg tctattgttg tcagagaaca tatgcatatg
 7081 atctcctctc ttaaatttat gaagacttgt tctgggcccc ggcatgtgct ctatcttgat
 7141 gaatgtattt tgtggtcttg aaaagaatgt atgttctgaa gttgtttcat ttaaaagtag
 7201 caataataaa ttcaataatg ttaatgtatt taacattgta tataatgcta acataatgaa
 7261 gtaaaaaaac aaacaaactg agaaaccaat aacatctata ttttccaaac ataatttagt
 7321 gagtagagtg gcattgtttt ttacatttt acaaatattt tcaatgttag gcttagtcgg
 7381 agatagctgg atctggcttt caatctgttg taatatcaca tatcttatag cctctagaaa
 7441 actctgctgt atacttataa gtgaataaaa gaaaaaaagg caaataaagt cttatgatta
 7501 aaaaaataat aataaagtca tgattttatg aaaatagttc tggctttgtg gacctcctat
 7561 aagggttta ggaaaccttc aggggtccct ggctcacact ttaggaacca ctgatacatg
 7621 tctttattga ttatttttg cctaattgct cctatagata gagaggtagc aagatctact
 7681 gtattgtgta attctccgat tacttatgta aatatttcct ttatgttttt tgaagcttta
 7741 ttatttgatg catatatatt tatgccatgc ttattcgctc agtcgattcc ctgggtcagg
 7801 gagatcccct ggagaaggaa atggcacccc actccagtat tcttgcctgg agaatcccat
 7861 ggatggagca gcctggtagg ctacagtcca tggggtcgaa cagagtcgga cacgactgag
 7921 cgagctcact cactttcact tttagtctcc cagtcatatc caattctttg tgacctcatg
 7981 atctgtagtc tgccaggctc ctctgtctgt ggggattctc caggcaagaa tactggagta
 8041 ggttgctagg ccctcctcct ggggatcttc ccagatgctg gaccagatca gatcgaaccc
 8101 aggtctccca cattgcaggc agattcttta ctgtctgagc caccagggaa gcatatatgt
 8161 ttatagttat ttataattag tatgtctttc tgattgattg acccttaat aattatggaa
 8221 tagcttctt gatctctggt atccctcttt gtctggggtc aaatataatg ccttcagcct
 8281 tttattctat attaacacaa tgtattttt catgctttt atttattttt tattttaaa
 8341 ttaattatt tatttaatt ggaggctaat tactttacag tattgtagtg gttttgcca
 8401 tacattgaca tgaatcagcc atgggtatac atgtgttccc catcctgaac ccccctccca
 8461 cctccttccc catcccatcc ctcagggtca tcccagtgca ccagctctga gcatcctgtc
 8521 tcatgcatca aacctgggct ggcgatctgt ttcacatatg ataatataggg tgtttcaatg
 8581 ctattctctc aaatcatccc accctcgcct tctcccacag agtccaaaag actgttctat
 8641 acatctgtgt ctcttttgct gtctcgcata tagggtcatc attaccatct ttctaaattc
 8701 attagtatac tgtattggtg ttttcattc tgacttactt cactctgtat aacaggctcc
 8761 agtttcattc accttattag aactgattca aatgcattct ttttaacagc tgagtatata
 8821 tgtaccacat ctttcttatc cattcatctg ctaatggaca tctaggttgt ttccatgtcc
 8881 tggctattat aaacagtgct gcgatgaaca atggggtaca cgtgtctctt tcaattctga
 8941 tttcctaggt gtgtatgccc agcagtggga ttgctgggtc atatggcagt tctagttgca
 9001 gtttttatt catgcttttt aaaatttgaa atgtagacag cacataattg agtctttttg
 9061 tatttattct gaaaatcttt gcttttaatt gaggtgttca gtttattaat attaatgta
 9121 atgttaaata cccgtctact gaggtccaca ttttaatatt tattttgttt tgtcccttt
 9181 tggttttttg ttcctctgtt cttcctttta attctttaaa ttttttaaga tgctgcttta
 9241 acttaaccat ttaagctttc ctcctaccct accctatggg tgttttctgt atcttgagat
 9301 taacgcattg cctgagactt agcaggcatt gaataaaagt tgggggatg attcaagcag
 9361 gtcttcatta catctgaatc catcccagat taacgtgaaa gaaagacag cccttttcca
 9421 agattaggga ataggagatt caggctctta tttctaccca aggccattga ctggctgaca
 9481 gaatggatga tccgcttctt gggttttctg tttgctactt gtgaggttgg gtttgtcccc
 9541 atcatgcaat gtcagttcag tctcatttat caggtgcacc catcagaaac acagatgact
 9601 gatctgtttg tgtgagggca gtctcagctc cctccagtga agcagacaat tgcctcacgt
 9661 ctcctggcgt ccttcccaga agcttctgca atttgccagg agagacttaa gtgggttact
 9721 tgcataagga agccaggtcc cggtgttggg attatcactg tctccctgtg ggtggcagga
 9781 ttccgagtgg ctgtccagat tgttctgctc cattccttgc ctgctcagtc cctgcagtc
 9841 agaatggagc catatttcta agttctcttg aatagagttg ctttagtctg tcccagccct
 9901 gtgtgtccat aggaccgggt cttggccatg tgacatggcc ctcagaggcc tgcaaggagc
 9961 ttgaccaaga cttgctgact gacgctcacg tcttctagac tcagcccag tgaggtccct
10021 gggatgttca gaaaggccat tggcgagggt aggatgccag cactggggac agtggttacc
```

Figure 1 (Continued)

```
10081 tgtggaggga gggatggggt tgccagcagg ggaggggtac gggtgcttca ccatggaagt
10141 gcctgatttc ttaagcggct tcttgataca caggtgtttc ttgtatcatc ctctctactt
10201 cctgtgtctt aagtatttca tcacaggttg tttgcagagg gagtcagtga ggcctggtta
10261 catattcctg ccattgatga gcggcctgag agctggtgtg gagagaaatt gcctctctct
10321 cctgagagaa tctcactgct tttgtgtccc cagtggcccc gactctctct gtgtctcatt
10381 tccggttggt tagctgagct cacagtgacc aacctggtta agcatgttag ggaccttcac
10441 cacctgaaga aaacccoctt ccctgaggag aggctgccaa gcctggtagt caggacaaag
10501 cccacggacc agaggcttct cacgaggctg tgcccgtgag gttggggctg agagctgctc
10561 catctgcctt tcatcccctc atgtaaccca ttaaccataa ctgacttccc tcggggccca
10621 atggtgccag gcagcttcct gagcattttc tgtctcatca cttagcagca gccgctgaag
10681 tagatgcctc atgatgctcc ccttttacag atgggaaaac tgaggcatag gagagtgggg
10741 tgacttgccc aagttcacca cctggtgaat ggcggggttc acttcagacc agacatggtg
10801 gctccaagcc agaccatgca ttgggtgagg caggctaagt aggggggttgg ccagggcagg
10861 cttctcctca gctgtccccc aggcttccat ctccccactc cctgagagga gctcagagtc
10921 gggccacagg ggccagagtc ttctcatcta cgggccccgt tgctgtggaa cctgactggc
10981 cgctggtcag acatgtcccc tcgagggtct tgcctccaga acagatgggc tcccggctgg
11041 accggggagg tcatggtcgt ggtgtcctgt ccctcctcc agctcagttt gcccagctgg
11101 cccagctgaa cccccaggag cgactgagcc gggagacggc cctccagcag aagcaggtgt
11161 ccctggaggc ctggctgcag cgcgaggccc agacgctgca gcagtaccgc gtggtgagtg
11221 ggctcagcgt ccctcccctc ccgcaggggc agtgacaccc tgagctgtcc tggggaccct
11281 gagggaggca gagagccagg aggagagcgg gacccagcag agcaggaggc ccgggccttc
11341 ttcctcatgg ggcctgaggg ggagagtcgg tctgggagga ggaggccctg cagggctgtt
11401 ctgagagccc agaagggccg gctgagccac cgcccgaccc tcaggagctg gccgagaagc
11461 accagaagac cctgcagctg ctgcggaagc agcagaccat catcctggat gacgagctga
11521 tccagtggaa gcggcggcag cagctggcgg ggaacggagg gcccccccgag ggcagcctgg
11581 atgtgctaca gtcctggtac caggggtggg gggcggggag gggcaggcag cagagtggtg
11641 ctgccagctg ctgtttgcgc ccacgtctac atgagcagct ggctccctct gtctgggcgc
11701 gggtcttatc ccaccagtgg tgtgtttggt gctgacaccg gtgtccctt ctgtgccccc
11761 tccccctggga ggatgctggg gtggggccag gtggcaaagt ggcgctcagg ctggttggac
11821 cccagtcagt gtcgctcctc ctgggtgttt ctctggtttt tttggaaggc agggcatctc
11881 tgctgtgccc agtgcacagg cgaggtggct cgggcaccag gccttcctgg gggtggagct
11941 gggtgtgggc cttgtccccg cctgggcgcc tgccagcttc tggcctggag gacggggggtg
12001 aagcccgtgt ccttcccttg ggccctgggg ctcgggttca ggtgtgagaa gttggcggag
12061 attatctggc agaaccggca gcagatccgc agagccgagc acctctgcca gcagctgccc
12121 atccccggcc ccgtggagga gatgctggct gaggtcaacg ccaccatcac tgacatcatc
12181 tcagccctgg tgaccaggtg actcctggcc acgcccgct cccatctggt tgccctgggt
12241 tgggggcagc agggtctttg cagatgggga gctctggctt aaatccttca gtttctgcct
12301 cacaccctcc tcccatccct ctccatcccc tgttgctatg gcctcttgct gtcgacctca
12361 cccagtcatt ctcgtggaca ctacacgggc atttgtctcc tgcaactcct ttcagctgct
12421 gagttccttt tactgcctcc cttcccgcca gctccccctga ctcacagtgg ccccaggggag
12481 ggtggactgt ccgcaaaccc tcccttcacc tgctcagcct ggtgcaaggc agcctcccca
12541 cgtggaaggt ggggccagag tcctgtcccc tgaagtgtct cctgtcccctt gtgtctccgc
12601 agcaccttca tcatcgagaa gcagccccct caggtcctga gacccagac caagttcgcg
12661 gccaccgtgc gcctgctggt gggtggggaag ctgaacgtgc acatgaaccc ccccccaggtg
12721 aaggccacca tcatcagcga gcagcaggcc aagtcactgc tcaagaacga gaacacccgc
12781 aagtatgctg cccgctcctt catctgccct cccccagctc agcctctgct ctgtagctgg
12841 ggtcccaggt gatgaggaca cacggggcct cccactcttt gtctagcatt gcaatgacag
12901 atgactctgt ctgtctgggg gtattcctcg cacacagagc aaatcaagga cttcactatt
12961 agggtgtccc aggatctgtg ctgagcactg gcacagtgct gggatccaca ccaaacttgg
13021 ctccatcacg gccaacctt taggctagca ggcagcagac gtgagaattg attacttgct
13081 ggcatgtgaa aagagagacg actgggcac catgaaagtg ggtcatggag ggggtgggac
13141 agaatgacag ctagttcaa ggctgcgggg tgactaggag gagatggtga acgggcgtgg
13201 agagggcaga cgttcgggca gagagaacac gggcctgtct ggagaggag cagacaaagg
13261 gcgtggtgga tggagaaccc ggggtgaggt cctgggatta ggccaggcca cccgtgaagg
13321 gcgtggagt gagtgaagga gggcgggaat gagtgagggg agagactggg tcctgagtac
13381 tgaggcccac tgtgtgctct gggctaggga tgacgaagat gacgaagagt tctcactctc
13441 ttagagcctg ccttttgggct gggaacaaga cagtcatata ctcttaaaaa tcaggcagcg
13501 tcagaaggca atagattcta gacagaaaat taaagccaag caatatcaca gcgcctggat
```

Figure 1 (Continued)

```
13561 agatgttgca acagcacatg gatggccaag gagggccttt ctgaggatct atttgagtgg
13621 agacctgaat gagaaagtca agaatgcaac aggagaattt gcctggtggt ccactggtta
13681 agactccacc ttccaataca ggggtatgg gttagatccc cggttgggaa actaaggtcc
13741 catatgcctc ggggtacagc cagaactttt taaaaaattt aaaaaatagt aaagtgcaaa
13801 atgcattact taaaaaaaga atgtaacagg aaggcaagta caggagtccc caggcagcac
13861 tgagcttgtg tgttcagcaa acagacaaga tactgtgggc ttgcttgttc tgaatgaggg
13921 gagggagcc cagtgaggcc agggcagggg ttgatggcat ggatcttgtt aggctgaggt
13981 catgatttt atgtcaagtg ggctagaagc tgccaaaggc ccccacgtca atcttgacgc
14041 ccaaggaact ttaacattgg ccccacccLt ggggctttgc tcggatgctc tcaggttgat
14101 gaggaaagac agcccagagg aacgctctta gggaggggt caggggctgc tgtgggcct
14161 tctggagaag ctggggccca gggtgcatac aggacagtgc tctgggcctg ggcccagcgg
14221 agacgggttc ccctctgctt ggcagtgagt gcagcgggga gatcctgaac aactgctgtg
14281 tgatggagta tcaccaggcc acaggcaccc tcagcgccca cttcagaaac atggtgagga
14341 cagggccgg cccgagctgg gaggtctgtc cagagctgag tcctgagtcc tcgtaacctg
14401 ccacgttccc ctcgtccct tttgatctcc caccctgcag tccctcaaga ggatcaagcg
14461 agctgaccgg cgaggtgcag agtctgtgac ggaagagaag ttcacggtcc tgtttgagtc
14521 tcaattcagt gttggcagca atgagcttgt gttccaggtg aaggtgaggc ctggctcccc
14581 tgtccctgc aggccaccca gctgacttgg gaaagccaga gactggaatc cttgcatacg
14641 ctcagtccag ttaccgcatg atgctctcag aaaacctaat ttcactctgc tggtgcttat
14701 ttgctagatt gtaatctggc acctgggctt ccctggtggc tcagatgca aagaatccac
14761 ctgcaatgtg ggagacctgg gtttgatccc taggttggga agatcccctg tgagttaacc
14821 cactccagta ttcttacctg gagaatcacc atggacagag gagcctggcg ggctagagtt
14881 catggggtcc caaagagtag gacacgacag agtaggacac gactgagtga ctgagcacag
14941 acagcaatct ggcacccacc ctcaggattg aggcaatggc caaaagaaa tgggctgtgt
15001 tttttgttta ttctgctttt ggttttgctg gaagggggct gagaatggc ggtcaggtgc
15061 ctcccccaag tggagggcaa gaccagggtc ataggccctc atccctcatt ccctggattc
15121 ccgtagaccc tgtcccttcc cgtggttgtc atcgttcatg gcagccagga ccacaatgct
15181 actgccacgg tgctgtggga caatgccttt gctgagccgg tgactccccg tgggaccccc
15241 acctcagccc cagcccctca gaggttccca gggccagccc caacccccag ggctcctgct
15301 gagtggtctt ctcccaccct tgggccaaac cagtggtcag ggggcagctg gtgtgagcgc
15361 cctgccctca gcacgacctc agctctgtct gggctccagg tcacgggact ggggtctcct
15421 aggtctgtga gcttggtgct tggaatctgg ccctgatct ctgctcccag ggctccgttc
15481 tgggtctcta ccctatata cccgtccctc tgctcctgcc ccccgtttct ttccattgtg
15541 gttttgtctc ctttcctgga tctttctcac tccctctgc ctcttggtat ctgtgtgtgt
15601 gtgtgtgtgt gtgtgtaaat atctcctatt acctcaatct tttcccttt ctttctctccc
15661 tctcagggca gggtgccgtt tgcggtgccc gacaaagtct tgtggccgca gctgtgcgag
15721 gcgctcaaca tgaaattcaa ggccgaggtg cagagcaacc ggggcctgac caaggagaac
15781 ctggtgttcc tggcgcagaa gctgttcaac agcagcagca gccatctcga ggactacaac
15841 ggcatgtccg tgtcctggtc ccagttcaac cgggtaaggg acgcattgcc tgctggctgc
15901 ctgggactat ctctacccct ccccacctca cagacaggca cctggtccat gggccccctc
15961 caccccaga ccctctcct acaaccagga gagatggggg ctggtgcccc aaggagtgga
16021 gacagccatg agacccgagg caagactttg gaaagaaccc agagctggaa gtcagggtcc
16081 ccgggctctg gtcctcaaca tgttacctca tttgccaggc cccttccgtt ctctgcatcg
16141 cacttttccc atctgtagaa tgaagggtt gggcaggaat gactttggag gtctcatcca
16201 gcttggacag tttcttgcac ctttgacccc ctccatggga ttgtcccaga tccctgtgtc
16261 tgagaggatg ggcttcccag gtagcgctag tggtaaagaa cctcctgcc aatgcggag
16321 ataaaagaga cgtgggttcg atccctgggt taggaagatc ccctggagga gggcatggca
16381 acccactcca ctattcttgc ctggaaaatc ccatggaccg gaggctggtg ggctatagtc
16441 cataaggtca caaagagccg gacacgattg aagcgacttg gcacacaggc actgggtgag
16501 gacacagggg caccaagtgt tccctggacc acctgagatg atggggacac aagccctaac
16561 ctgggctttc ccgggcaccc tcaggagaac ttgcccggct ggaactacac cttctggcag
16621 tggttcgacg ggtcatgga ggtgctgaag aaacatcaca agccccattg gaatgacggg
16681 tgaggcatgg cgggtgggag gtcggggctc aggggacagt ggctggtggc ccagcagtga
16741 ctctgtgtgc tccatgcacc cagggccatc ctaggttttg tgaacaagca acaggcccat
16801 gacctgctca tcaacaagcc cgacggtacc ttcttgttgc gcttcagcga ctcagaaatt
16861 gggggcatca ccatcgcctg gaagtttgac tctcgtgagt tccctgcatt gcccacactc
16921 ccgccccagt ggctctgttt ctcatttcct cattcccatt ctccatcagg cctgtatcct
16981 tagaaggggt ccagtgggaa agatgggaac tgagcttgga gggtgggtgg agtgttgttc
```

Figure 1 (Continued)

```
17041 aaatacccag tctctattgg tttcctcttg ggagaaccta acatcactac cccccacagc
17101 ctccagaact gctgagcgag tccttctttg tcctgaccca gacttgttgg tatctgctcg
17161 cccgtggtca cttccttgcc ctgtgctgag aacaggggtg gggtagcagt gcaggctttt
17221 acctggatgt ctccacaagc ctggccccca gccctacagc tccaatcctc ctcctgtggg
17281 cagtgggttg tgaaaatgag cttggccttt tcacagctga ccgtaacctg tggaatctga
17341 agccattcac cacgcggat ttctccatcc gatccctggc cgacaggttg ggggacctga
17401 actatctcat ctacgtgttt cccgaccggc ccaaggatga ggtcttctcc aagtactaca
17461 ctcctgtgct tggtgcgtct gcccaacact cctcccaaca cactcccggg gctaagcagc
17521 gggtacaccc caggaagagc ccaggggccc tttcccctgt gagggctggt ccgtgggatg
17581 gcacaaggca cgcagagggg atttcagggc tccgtgcacc cagggccatc ctaggttttg
17641 tgaacaagca acaggcccat gaagcggaaa ccccgaccta gctttcttcc ctgcaaagca
17701 aacactgagt gcactccctt ctgcgccctt ggaggaggag gcggctgcag tgtaggggga
17761 ggagcaggat cacgcagacc cacagataat gcacggctcc catcttaatc aactgctctc
17821 accoctctcc accctcaaac ctgccctcac agttgagggt aggaagcaaa atggacaggt
17881 ttttttctct tcaacctggc cccactcctt tggttgggtt tgttcctcgg tgtggactct
17941 gtttccttgg caggggtggg gacggggaga gaggaagcca agggccagga aaggaagcgg
18001 gacatgggat gagactgaaa ccagaggtct gggggtcac ctggtgactg tcagcaggtg
18061 ttcaatgggt ctgtgggaaa tcttatccct gatgagcccc gtggcattgt ggggagtggg
       [gap 470 bp]
18591                                                                gccacagatc
18601 aagcaagtgg tccgcagta agtgtccggg cccagcgctg gtctccagct gcctcttttc
18661 tcctcccgc gcggctccac ctggctctcc tcaccccca ccgcctcccc tcctattccc
18721 tccccacccc aacttggccc agccctgggg aggggaactg ggcgtggtca caagggcgg
18781 gtacccaggg ccccgcccct gcaccggagc cctaggctca ggggccagtt gtccttccac
18841 acctgagaaa gacacgaagg tgccccgag ccctcccg ctgaggctcc gcttcctcc
18901 acaggtttgt gagcgcctct gcagactctg ctggaagcaa cgccacctac atggaccagg
18961 ctccttcccc agccgtgtgc ccccagcctc actataacat gtacccacag aagtaggttg
19021 tgttctcatg cagctccatg tacccacaga agtaggttgt gttctcatgc agctccgggg
19081 ggaggaaccc agagggctaa tgggcaagga caccagagct cctctccgtc tgagaccacc
19141 caggccaggt gggcttgggt atatgcccag gtgcagggtg gatgagatca gccaaccagg
19201 agcacagagc attgtgaaat agcaggaccc ttgctctggt gctgagtagc tgtgtgacct
19261 tgggaaatt atggagcctc tctgatgctc agtttcctta tctgtaaaat ggaggcaaga
19321 gtacctacca catgggactg gggtcaggct caagcaagag actgcaggta atgcatttag
19381 cccaggtaag gctgttgtaa tggcttgata cagagtatct ctgggtggtg gtggttctta
19441 ggagttgtgt gggaacagga catgtctctc ctctctgaag ttcccagaga agaaaaltca
19501 ttctcttcc agccaagggt ggcctactgc catgggatga ccacaggctt gggagtcaca
19561 aaactggaat tccagtcctg actccacctg cctaccaggt ggctctgaac aagcttccta
19621 acatggttga gcctcagttt cttcctcagt ggctgtgggg attggcataa agtggttgaa
19681 aggcccaggc cttcataggt gctcagtgtc tcgtgcctga gatctcatgg gcagagctcc
19741 ttcacccaac cacctgtttt tacagaggag ggcagggaca gggaaatga attccctgag
19801 atccctcagt gagcttgtga gtgatgagac tagaaccggg gtgtcttccg acaaactagt
19861 gactgactga ttcagcttgg tggtgcgggc atctagccag agcacgtcct gttcccatga
19921 gactgaacgg ggatcaggct gggcgctgtc ccccaggagc ctgggctct gcggcaggcc
19981 agctccctct gataccctc tccccctccc agccctgacc cggtgctcga ccaggatgga
20041 gaattcgacc tggacgagac catggatgtg cccggcacg tggaagaact cctccgccgc
20101 ccaatggaca gtctggagcc ctctctcccc ccgcccactg gtctctttac ccccggcaga
20161 ggctcgctgt cctgaatgtt tgttcgaaca ctgcactcct ctgtggaaac aatccccagt
20221 gtgcagggtc ctattcattg tgattttgta tttgtatctc tgtgcatact gatgcctttg
20281 caggcagccc atgtacacat gtagat
```

METHODS AND COMPOSITIONS FOR IMPROVED FERTILIZATION AND EMBRYONIC SURVIVAL

CROSS-REFERENCE TO RELATED APPLICATION

This application also claims priority to U.S. provisional patent application No. 60/986,238, filed Nov. 7, 2007, entitled "METHODS AND COMPOSITIONS FOR IMPROVED FERTILIZATION AND EMBRYONIC SURVIVAL," which is incorporated herein by reference in its entirety.

GOVERNMENT INTEREST

This invention was made with United States government support awarded by the following agencies: USDA/CSREES 05-CRHF-0-6055. The United States government has certain rights in this invention.

FIELD OF THE INVENTION

The present invention relates to a method of genetic testing for improved fertilization rate and embryonic survival rate in animals, especially cattle.

BACKGROUND OF THE INVENTION

Dairy cows are significant investments for dairy farmers, and enormous efforts, such as animal breeding and artificial insemination, have been and continue to be invested in breeding programs to improve the animals. Typically, for unknown reasons, artificial insemination in dairy cattle is successful only 30-35% of the time. However, it is understood that both biological and environmental factors affect fertility rate. Some environmental factors such as heat and lack of precipitation, can cause stress in cattle and can decrease the fertility rate to 10-15%. Commercial artificial insemination operations often shut down in July and August due to the drop in fertility caused by the hot, dry weather. It is also known that certain bulls are more fertile than others due to their genetic makeup. Identifying highly fertile bulls, however, is a time consuming and expensive process. It can take 5-10 years of tracking the attempts of artificial insemination using semen from the bulls before they can be certified as quality bulls.

There is thus a need for a method of genetically evaluating the bulls, e.g., by genetic testing, to enable a quick and accurate evaluation of its fertility as well as the survival rate of embryos conceived therefrom. Genetic testing of the bulls to determine their fertility and embryo survival rate can lower the high cost of the traditional, progeny testing methods, by-passing the need to produce live birth.

There is further a need to ensure that the dairy cattle have highly desirable productive traits, such as milk fat content and protein content. In this regard, traditional breeding techniques involve the studying of sire progenies, and evaluating their traits including milk production ratings (transmitting abilities) to guide further breeding. This standard technique is similarly time consuming and costly, requiring years to evaluate the true genetic value by progeny testing of each bull. Many cows must be bred and give birth to offspring. The females must be raised, bred, allowed to give birth and finally milked for a length of time to measure their phenotypic traits. Furthermore, selection based purely on phenotypic characteristics does not efficiently take into account genetic variability caused by complex gene action and interactions, and the effect of the environmental and developmental variants. There is thus a need for a method of genetically evaluating cattle to enable breeders to more accurately select animals at both the phenotypic and the genetic levels.

Marker-assisted selection can lower the high cost of progeny testing currently used to improve sires, since young bull progeny could be evaluated immediately after birth or even before birth, and those young bulls that are determined by genetic testing to have undesirable markers would never be progeny tested, for the presence/absence of the marker. Therefore, there is also a need for genetic markers for such marker-assisted selection process.

The signal transducer and activator (STAT) proteins are known to play an important role in cytokine signaling pathways. STAT proteins are transcription factors that are specifically activated to regulate gene transcription when cells encounter cytokines and growth factors, hence they act as signal transducers in the cytoplasm and transcription activators in the nucleus (Kisseleva et al., 2002). In mammals, STATs comprise a family of seven structurally and functionally related proteins: STAT1, STAT2, STAT3, STAT4, STAT5A and STAT5B, STAT6 (Darnell, 1997). The seven mammalian STAT proteins range in size from 750 to 850 amino acids. The chromosomal distribution of these STATs, as well as the identification of STATs in more primitive eukaryotes, suggest that this family arose from a single primordial gene (Chen et al., 1998). In addition, STATs share a number of structurally and functionally conserved domains.

The STAT5 protein is also known as the mammary gland factor. This protein was initially identified in the mammary gland as a regulator of milk protein gene expression (Watson, 2001). STAT5A is a member of the interferon-tau (IFN-tau) and placental lactogen (PL) signaling pathway, which is involved in signal transduction within a variety of cells, including the uterus and mammary epithelial cells. The uterus is exposed to IFN-tau and PL, as well as many others hormones including estrogen, progesterone, and placental growth hormone. The PL stimulates the formation of STAT5 homodimers, which in turn induce the transcription of the bovine uterine milk protein (UTMP) and osteopontin (OPN) genes (Spencer and Bazer, 2002; Stewart et al., 2002; Spencer and Bazer, 2004). In previous studies, the present inventors showed that the UTMP (Khatib et al., 2007a) and OPN (Leonard et al. 2005; Khatib et al. 2007b) genes have surprisingly strong effects on milk production and health traits in cattle. Furthermore, the present inventors showed that STAT1—also a member of the IFN-tau and PL signal transduction pathway—is associated with milk composition and health traits (Cobanoglu et al., 2006).

Studies in mouse have shown that STAT5 is involved in both milk production and fertility; STAT5 knockout female mice fail to lactate (Miyoshi et al., 2001). Also, it has been shown that disruption of Stat5 leads to infertility in females as a result of small-sized or a lack of corpora lutea (Teglund et al., 1998). Because the primary source of progesterone is the corpora lutea of the ovary, lack of development of corpora lutea would have significant effects on the establishment of pregnancy.

Given that STAT5A is a member of the IFN-tau and PL signal transduction pathway, which is very important in both milk production and initiation of pregnancy, and that other genes in this pathway have been found to be associated with milk production and health traits, the present inventors investigated if STAT5A variants are associated with milk production and reproduction traits in dairy cattle.

SUMMARY OF THE INVENTION

The present inventors investigated the effects of association of the signal transducer and activator of transcription 5A (STAT5A) gene with fertilization rate, embryo survival, and milk production in cattle. Using the DNA pooling sequencing approach, a total of 12 single nucleotide polymorphisms (SNP) were identified, one exonic and 11 intronic. For the study of association of these SNP with embryo survival, a total of 1551 embryos were produced from 160 cows and 3 sires. Significant associations with embryo survival were found for 7, 5, and 2 SNP for embryos produced from sires 1, 2, and 3 respectively. The association of fertilization rate with STAT5A polymorphisms was also studied in more than 2300 oocytes. Significant associations were found for 6, 2, and 2 SNP for sires 1, 2, and 3 respectively. To determine if embryonic losses had occurred prior to the blastocyst stage, 145 of the surviving embryos were harvested at day 7 of development and genotyped for the exonic SNP12195. A significant segregation distortion was observed in oocytes produced from two sires carrying the same genotype. While not willing to be bound by any theory, the inventors believe that most likely STAT5A has two mechanisms by which it affects embryo death. One is a pre-fertilization mechanism involving sperm factors that cause low fertilization rate. The second is a post-fertilization mechanism that causes incompatibility between the male pronucleus and the oocyte, which in turn leads to death of the embryo before the blastocyst stage. Association testing of SNP12195 and SNP14217 with milk composition revealed that allele G of SNP12195 was associated with a decrease in both protein and fat percentages. However, SNP14217, in intron 9, showed no significant association with milk production or health traits. It is worth noting that the G allele of SNP12195 was also associated with low embryo survival, making this SNP an attractive candidate for marker assisted selection in dairy cattle.

Based on the results, the present invention provides an isolated nucleic acid molecule comprising at least one polymorphic site selected from the group consisting of position 3117 ("SNP 3117"), position 12195 ("SNP 12195"), position 13244 ("SNP13244"), position 13319, ("SNP 13319"), and position 13516 ("SNP 13516") of SEQ ID NO: 1 (the bovine STAT5 gene), and at least 8, 9, 10, 11, 12, 13, 14, 15, 16 or 17 contiguous nucleotides or bases of SEQ ID NO: 1 adjacent to the polymorphic site, wherein the nucleic acid molecule comprises a guanine at position 3117, a cytosine at position 12195, a guanine at position 13244, an adenine base at position 13319, or a guanine at position 13516 of SEQ ID NO: 1. It is recognized that SEQ ID NO: 1 is already known, and the nucleic acid molecule therefore does not encompass one that consists of SEQ ID NO: 1.

Preferably, the nucleic acid molecule which comprises at least 15, more preferably at least 20, still more preferably at least 25, contiguous bases of SEQ ID NO: 1 adjacent to the polymorphic site. In one embodiment, the isolated nucleic acid molecule comprises not more than 1,500 nt, preferably not more than 1000 nt, more preferably not more than 900 nt, more preferably not more than 800 nt, more preferably not more than 700 nt, preferably not more than 600 nt, more preferably not more than 500 nt, preferably not more than 400 nt, more preferably not more than 300 nt, more preferably not more than 150 nt., preferably not more than 100 nt., still more preferably not more than 50 nt.

The nucleic acid molecule preferably contains the polymorphic site which is within 4 nucleotides of the center of the nucleic acid molecule. Preferably, the polymorphic site is at the center of the nucleic acid molecule.

In another embodiment, the nucleic acid molecule contains the polymorphic site which is at the 3'-end of the nucleic acid molecule.

In another embodiment, the nucleic acid molecule contains the polymorphic site which is at the 5'-end of the nucleic acid molecule.

The present invention also provides an array of nucleic acid molecules comprising at least two nucleic acid molecules described above.

The present invention further provides a kit comprising a nucleic acid molecule described above, and a suitable container.

Also provided is a method for detecting single nucleotide polymorphism (SNP) in bovine STAT5A gene, wherein the STAT5A gene has a nucleic acid sequence as depicted in of SEQ ID NO: 1 and SEQ ID NO: 2, the method comprising determining the identity of a nucleotide at one or more positions 3117, 12195, 13244, 13319, and 13516, and comparing the identity to the nucleotide identity at a corresponding position of SEQ ID NO: 1.

In another embodiment, the present invention provides a method for genotyping a bovine cell, using the method above. Suitable bovine cell may be an adult cell, an embryo cell, a sperm, an egg, a fertilized egg, or a zygote. The identity of the nucleotide may be determined by sequencing the STAT5A gene, or a relevant fragment thereof, isolated from the cell.

In a further embodiment, the present invention provides a method for testing the fertility of a bull cattle, the method comprising collecting a nucleic acid sample from the cattle, and genotyping said nucleic sample as described above, wherein a bull having a STAT5A gene sequence which comprises a guanine at position 3117, a cytosine at position 12195, a guanine at position 13244, an adenine base at position 13319, or a guanine at position 13516 of SEQ ID NO: 1 is selected for breeding purposes.

Preferably, a bull having a STAT5A gene sequence which is homozygous at one of the above described polymorphic site is selected for breeding purposes.

Preferably, a bull having a STAT5A gene sequence which comprises a cytosine at position 12195 is selected for breeding purposes.

Preferably, a bull having a STAT5A gene sequence which is homozygously C at position 12195 is selected for breeding purposes.

Preferably, a bull having a STAT5A gene sequence which comprises a guanine at position 3117, a cytosine at position 12195, and a guanine at position 13244 is selected for breeding purposes for improved fertilization rate.

Preferably, a bull having a STAT5A gene sequence which comprises a cytosine at position 12195, an adenine base at position 13319, or a guanine at position 13516 of SEQ ID NO: 1 is selected for breeding purposes for improved embryo survival rate.

Further provided is a method for selectively breeding cattle using a multiple ovulation and embryo transfer procedure (MOET), the method comprising superovulating a female animal, collecting eggs from said superovulated female, in vitro fertilizing said eggs from a suitable male animal, implanting said fertilized eggs into other females allowing for an embryo to develop, genotyping the developing embryo, and terminating pregnancy if the developing embryo does not have cytosine (C) at position 12195. Preferably, pregnancy is terminated if the embryo is not homozygously C at position 112195.

In a preferred embodiment, the present invention provides a method for selectively breeding dairy cattle, comprising selecting a bull whose STAT5A gene is hemizygously or homozygously guanine at position 3117, cytosine at position 12195, guanine at position 13244, an adenine base at position 13319, or guanine at position 13516, and using its semen for fertilizing a female animal. Preferably the bull is homozygous with regard to the above SNP site. More preferably, the female animal is also homozygous at the above SNP site, that is, homozygously guanine at position 3117, cytosine at position 12195, guanine at position 13244, adenine at position 13319, or a guanine at position 13516.

DESCRIPTION OF THE DRAWINGS

FIG. 1 shows the STAT5A gene sequence (SEQ ID NO: 1 and SEQ ID NO: 2) where the relevant polymorphic sites are shown in shaded text.

DETAILED DESCRIPTION OF THE INVENTION

Figure 2:
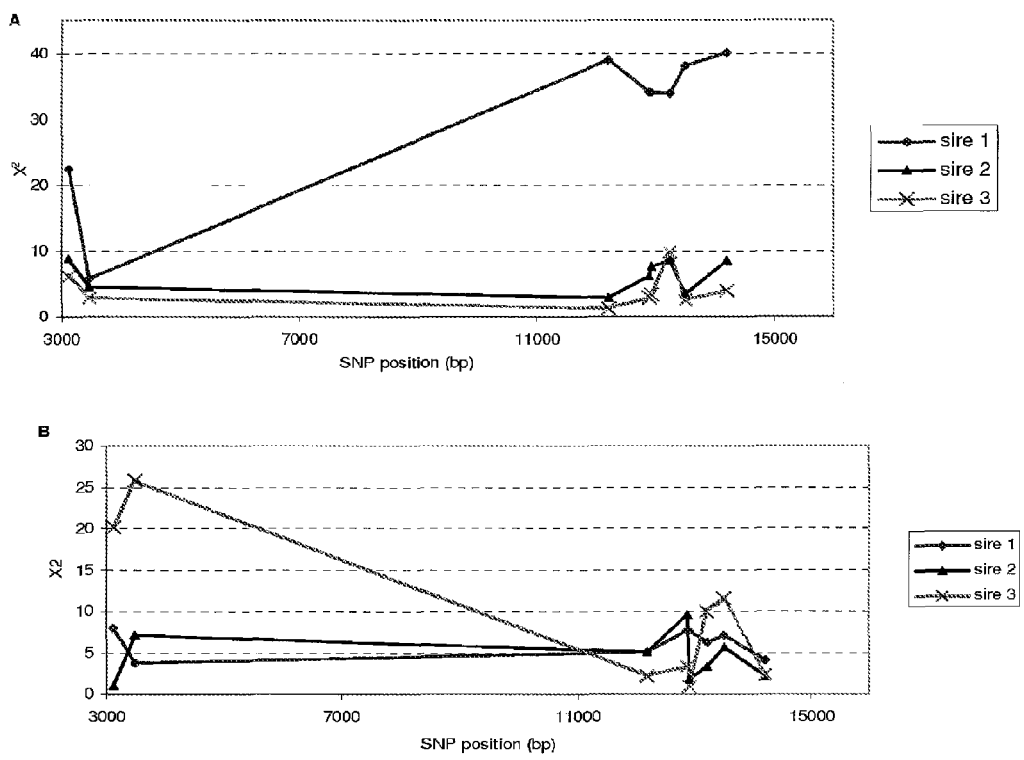
FIG. 2 shows Chi-square analysis of embryo survival rate (A) and unfertilized ova (UFO) (B) for sires 1, 2, and 3 with SNP3117, SNP3470, SNP12195, SNP12885, SNP12924, SNP13244, SNP13516, and SNP14217.

It has been found several positions of the bovine STAT5A gene are polymorphic. The term "polymorphism" as used herein refers to the occurrence of two or more alternative genomic sequences or alleles between or among different genomes or individuals. "Polymorphic" refers to the condition in which two or more variants of a specific genomic sequence can be found in a population. A "polymorphic site" is the locus at which the variation occurs. Polymorphisms generally have at least two alleles, each occurring at a significant frequency in a selected population. A polymorphic locus may be as small as one base pair. The first identified allelic form is arbitrarily designated as the reference form, and other allelic forms are designated as alternative or variant alleles. The allelic form occurring most frequently in a selected population is sometimes referred to as the wild type form. Diploid organisms may be homozygous or heterozygous for allelic forms. A biallelic polymorphism has two forms, and a triallelic polymorphism has three forms, and so on.

Polymorphisms may provide functional differences in the genetic sequence, through changes in the encoded polypeptide, changes in mRNA stability, binding of transcriptional and translation factors to the DNA or RNA, and the like. Polymorphisms are also used to detect genetic linkage to phenotypic variation.

One type of polymorphism, single nucleotide polymorphisms (SNPs), has gained wide use for the detection of genetic linkage recently. SNPs are generally biallelic systems, that is, there are two alleles that an individual may have for any particular SNP marker. In the instant case, the SNPs are used for determining the genotypes of the STAT5A gene, which are found to have strong correlation to longevity and milk production traits.

The provided sequences also encompass the complementary sequence corresponding to any of the provided polymorphisms. In order to provide an unambiguous identification of the specific site of a polymorphism, the numbering of the original STAT5A sequence in the GenBank is shown in FIG. 1 and is used throughout this disclosure.

The present invention provides nucleic acid based genetic markers for identifying bovine animals with superior breeding (such as fertility and embryo survival rates) and milk production traits. In general, for use as markers, nucleic acid fragments, preferably DNA fragments, may be as short as 7 nucleotides (nt), but may preferably at least 12 nt, 15 nt, usually at least 20 nt, often at least 50 nt. Such small DNA fragments are useful as primers for the polymerase chain reaction (PCR), and probes for hybridization screening, etc.

The term primer refers to a single-stranded oligonucleotide capable of acting as a point of initiation of template-directed DNA synthesis under appropriate conditions (i.e., in the presence of four different nucleoside triphosphates and an agent for polymerization, such as, DNA or RNA polymerase or reverse transcriptase) in an appropriate buffer and at a suitable temperature. The appropriate length of a primer depends on the intended use of the primer but typically ranges from 15 to 30 nucleotides. Short primer molecules generally require cooler temperatures to form sufficiently stable hybrid complexes with the template. A primer need not reflect the exact sequence of the template but must be sufficiently complementary to hybridize with a template. The term primer site, or priming site, refers to the area of the target DNA to which a primer hybridizes. The term primer pair means a set of primers including a 5' upstream primer that hybridizes with the 5' end of the DNA sequence to be amplified and a 3', downstream primer that hybridizes with the complement of the 3' end of the sequence to be amplified.

The term "probe" or "hybridization probe" denotes a defined nucleic acid segment (or nucleotide analog segment) which can be used to identify by hybridizing to a specific polynucleotide sequence present in samples, said nucleic acid segment comprising a nucleotide sequence complementary of the specific polynucleotide sequence to be identified. "Probes" or "hybridization probes" are nucleic acids capable of binding in a base-specific manner to a complementary strand of nucleic acid.

An objective of the present invention is to determine which embodiment of the polymorphisms a specific sample of DNA has. For example, it is desirable to determine whether the nucleotide at a particular position is A or C. An oligonucleotide probe can be used for such purpose. Preferably, the oligonucleotide probe will have a detectable label, and contains an A at the corresponding position. Experimental conditions can be chosen such that if the sample DNA contains an A, they hybridization signal can be detected because the probe hybridizes to the corresponding complementary DNA strand in the sample, while if the sample DNA contains a G, no hybridization signal is detected.

Similarly, PCR primers and conditions can be devised, whereby the oligonucleotide is used as one of the PCR primers, for analyzing nucleic acids for the presence of a specific sequence. These may be direct amplification of the genomic DNA, or RT-PCR amplification of the mRNA transcript of the STAT5A gene. The use of the polymerase chain reaction is described in Saiki et al. (1985) Science 230:1350-1354. Amplification may be used to determine whether a polymorphism is present, by using a primer that is specific for the polymorphism. Alternatively, various methods are known in the art that utilize oligonucleotide ligation as a means of detecting polymorphisms, for examples see Riley et al (1990) Nucleic Acids Res. 18:2887-2890; and Delahunty et al (1996) Am. J. Hum. Genet. 58:1239-1246. The detection method may also be based on direct DNA sequencing, or hybridization, or a combination thereof. Where large amounts of DNA are available, genomic DNA is used directly. Alternatively, the region of interest is cloned into a suitable vector and grown in sufficient quantity for analysis. The nucleic acid may be amplified by PCR, to provide sufficient amounts for analysis.

Hybridization may be performed in solution, or such hybridization may be performed when either the oligonucleotide probe or the target polynucleotide is covalently or non-covalently affixed to a solid support. Attachment may be mediated, for example, by antibody-antigen interactions, poly-L-Lys, streptavidin or avidin-biotin, salt bridges, hydrophobic interactions, chemical linkages, UV cross-linking baking, etc. Oligonucleotides may be synthesized directly on the solid support or attached to the solid support subsequent to synthesis. Solid-supports suitable for use in detection methods of the invention include substrates made of silicon, glass, plastic, paper and the like, which may be formed, for example, into wells (as in 96-well plates), slides, sheets, membranes, fibers, chips, dishes, and beads. The solid support may be treated, coated or derivatized to facilitate the immobilization of the allele-specific oligonucleotide or target nucleic acid. For screening purposes, hybridization probes of the polymorphic sequences may be used where both forms are present, either in separate reactions, spatially separated on a solid phase matrix, or labeled such that they can be distinguished from each other.

Hybridization may also be performed with nucleic acid arrays and subarrays such as described in WO 95/11995. The arrays would contain a battery of allele-specific oligonucleotides representing each of the polymorphic sites. One or both polymorphic forms may be present in the array, for example the polymorphism of position 12195 may be represented by either, or both, of the listed nucleotides. Usually such an array will include at least 2 different polymorphic sequences, i.e. polymorphisms located at unique positions within the locus, and may include all of the provided polymorphisms. Arrays of interest may further comprise sequences, including polymorphisms, of other genetic sequences, particularly other sequences of interest. The oligonucleotide sequence on the array will usually be at least about 12 nt in length, may be the length of the provided polymorphic sequences, or may extend into the flanking regions to generate fragments of 100 to 200 nt in length. For examples of arrays, see Ramsay (1998) Nat. Biotech. 16:4044; Hacia et al. (1996) Nature Genetics 14:441-447; Lockhart et al. (1996) Nature Biotechnol. 14:1675-1680; and De Risi et al. (1996) Nature Genetics 14:457-460.

The identity of polymorphisms may also be determined using a mismatch detection technique, including but not limited to the RNase protection method using riboprobes (Winter et al., Proc. Natl. Acad. Sci. USA 82:7575, 1985; Meyers et al., Science 230:1242, 1985) and proteins which recognize nucleotide mismatches, such as the *E. coli* mutS protein (Modrich, P. Ann. Rev. Genet. 25:229-253, 1991). Alternatively, variant alleles can be identified by single strand conformation polymorphism (SSCP) analysis (Orita et al., Genomics 5:874-879, 1989; Humphries et al., in Molecular Diagnosis of Genetic Diseases, R. Elles, ed., pp. 321-340, 1996) or denaturing gradient gel electrophoresis (DGGE) (Wartell et al., Nucl. Acids Res. 18:2699-2706, 1990; Sheffield et al., Proc. Natl. Acad. Sci. USA 86:232-236, 1989).

A polymerase-mediated primer extension method may also be used to identify the polymorphism(s). Several such methods have been described in the patent and scientific literature and include the "Genetic Bit Analysis" method (WO92/15712) and the ligase/polymerase mediated genetic bit analysis (U.S. Pat. No. 5,679,524). Related methods are disclosed in WO91/02087, WO90/09455, WO95/17676, U.S. Pat. Nos. 5,302,509, and 5,945,283. Extended primers containing a polymorphism may be detected by mass spectrometry as described in U.S. Pat. No. 5,605,798. Another primer extension method is allele-specific PCR (Ruao et al., Nucl. Acids Res. 17:8392, 1989; Ruao et al., Nucl. Acids Res. 19, 6877-6882, 1991; WO 93/22456; Turki et al., J. Clin. Invest. 95:1635-1641, 1995). In addition, multiple polymorphic sites may be investigated by simultaneously amplifying multiple regions of the nucleic acid using sets of allele-specific primers as described in Wallace et al. (WO 89/10414).

A detectable label may be included in an amplification reaction. Suitable labels include fluorochromes, e.g. fluorescein isothiocyanate (FITC), rhodamine, Texas Red, phycoerythrin, allophycocyanin, 6-carboxyfluorescein (6-FAM), 2',7'-dimethoxy-4',5'-dichloro-6-carboxyfluorescein (JOE), 6-carboxy-X-rhodamine (ROX), 6-carboxy-2',4',7',4,7-hexachlorofluorescein (HEX), 5-carboxyfluorescein (5-FAM) or N,N,N',N'-tetramethyl-6-carboxyrhodamine (TAMRA), radioactive labels, e.g. $^{32}P$, $^{35}S$, $^{3}H$; etc. The label may be a two stage system, where the amplified DNA is conjugated to biotin, haptens, etc. having a high affinity binding partner, e.g. avidin, specific antibodies, etc., where the binding partner is conjugated to a detectable label. The label may be conjugated to one or both of the primers. Alternatively, the pool of nucleotides used in the amplification is labeled, so as to incorporate the label into the amplification product.

It is readily recognized by those ordinarily skilled in the art that in order to maximize the signal to noise ratio, in probe hybridization detection procedure, the polymorphic site should at the center of the probe fragment used, whereby a mismatch has a maximum effect on destabilizing the hybrid molecule; and in a PCR detection procedure, the polymorphic site should be placed at the very 3'-end of the primer, whereby a mismatch has the maximum effect on preventing a chain elongation reaction by the DNA polymerase. The location of nucleotides in a polynucleotide with respect to the center of the polynucleotide are described herein in the following manner. When a polynucleotide has an odd number of nucleotides, the nucleotide at an equal distance from the 3' and 5' ends of the polynucleotide is considered to be "at the center" of the polynucleotide, and any nucleotide immediately adjacent to the nucleotide at the center, or the nucleotide at the center itself is considered to be "within 1 nucleotide of the center." With an odd number of nucleotides in a polynucleotide any of the five nucleotides positions in the middle of the polynucleotide would be considered to be within 2 nucleotides of the center, and so on. When a polynucleotide has an even number of nucleotides, there would be a bond and not a nucleotide at the center of the polynucleotide. Thus, either of the two central nucleotides would be considered to be "within 1 nucleotide of the center" and any of the four nucleotides in the middle of the polynucleotide would be considered to be "within 2 nucleotides of the center," and so on.

In some embodiments, a composition contains two or more differently labeled oligonucleotides for simultaneously probing the identity of nucleotides or nucleotide pairs at two or more polymorphic sites. It is also contemplated that primer compositions may contain two or more sets of allele-specific primer pairs to allow simultaneous targeting and amplification of two or more regions containing a polymorphic site.

Alternatively, the relevant portion of the STAT5A gene of the sample of interest may be amplified via PCR and directly sequenced, and the sequence be compared to the wild type sequence shown in FIG. 1. It is readily recognized that, other than those specifically disclosed herein, numerous primers can be devised to achieve the objectives. PCR and sequencing techniques are well known in the art and reagents and equipments are readily available commercially.

DNA markers have several advantages; segregation is easy to measure and is unambiguous, and DNA markers are co-dominant, i.e., heterozygous and homozygous animals can be distinctively identified. Once a marker system is established selection decisions could be made very easily, since DNA markers can be assayed any time after a blood sample can be collected from the individual infant animal, or even earlier by testing embryos in vitro if very early embryos are collected.

The use of marker assisted genetic selection will greatly facilitate and speed up cattle breeding problems. For example, a modification of the multiple ovulation and embryo transfer (MOET) procedure can be used with genetic marker technology. Specifically, females are superovulated, eggs are collected, in vitro fertilized using semen from superior males and implanted into other females allowing for use of the superior genetics of the female (as well as the male) without having to wait for her to give birth to one calf at a time. Developing blastomeres at the 4-8 cell stage may be assayed for presence of the marker, and selection decisions made accordingly.

In one embodiment of the invention an assay is provided for detection of presence of a desirable genotype using the markers.

The term "genotype" as used herein refers to the identity of the alleles present in an individual or a sample. In the context of the present invention a genotype preferably refers to the description of the polymorphic alleles present in an individual or a sample. The term "genotyping" a sample or an individual for a polymorphic marker refers to determining the specific allele or the specific nucleotide carried by an individual at a polymorphic marker.

The present invention is suitable for identifying a bovine, including a young or adult bovine animal, an embryo, a semen sample, an egg, a fertilized egg, or a zygote, or other cell or tissue sample therefrom, to determine whether said bovine possesses the desired genotypes of the present invention, some of which are indicative of improved milk production traits.

Further provided is a method for genotyping the bovine STAT5A gene, comprising determining for the two copies of the STAT5A gene present the identity of the nucleotide pair at position 12195.

One embodiment of a genotyping method of the invention involves examining both copies of the STAT5A gene, or a fragment thereof, to identify the nucleotide pair at the polymorphic site in the two copies to assign a genotype to the individual. In some embodiments, "examining a gene" may include examining one or more of: DNA containing the gene, mRNA transcripts thereof, or cDNA copies thereof. As will be readily understood by the skilled artisan, the two "copies" of a gene, mRNA or cDNA, or fragment thereof in an individual may be the same allele or may be different alleles. In another embodiment, a genotyping method of the invention comprises determining the identity of the nucleotide pair at the polymorphic site.

The present invention further provides a kit for genotyping a bovine sample, the kit comprising in a container a nucleic acid molecule, as described above, designed for detecting the polymorphism, and optionally at least another component for carrying out such detection. Preferably, a kit comprises at least two oligonucleotides packaged in the same or separate containers. The kit may also contain other components such as hybridization buffer (where the oligonucleotides are to be used as a probe) packaged in a separate container. Alternatively, where the oligonucleotides are to be used to amplify a target region, the kit may contain, preferably packaged in separate containers, a polymerase and a reaction buffer optimized for primer extension mediated by the polymerase, such as PCR.

In one embodiment the present invention provides a breeding method whereby genotyping as described above is conducted on bovine embryos, and based on the results, certain cattle are either selected or dropped out of the breeding program.

Through use of the linked marker loci, procedures termed "marker assisted selection" (MAS) may be used for genetic improvement within a breeding nucleus; or "marker assisted introgression" for transferring useful alleles from a resource population to a breeding nucleus (Soller 1990; Soller 1994).

The present invention discloses the association of the bovine STAT5A gene with fertilization success, embryo survival, and milk composition in Holstein dairy cattle. This is the first study in a livestock species to select a gene for association with quantitative traits based on a candidate pathway rather than position of the candidate gene. The death of embryos appears to occur much earlier than any other previously known naturally occurring embryonic lethal polymorphism in mammals. The molecular mechanisms that cause this early embryonic death have not yet been identified. Nevertheless, there is firm evidence that mutations in STAT5A are associated with embryonic lethality in cattle.

First, a trial was conducted with in vitro-produced embryos. The association between STAT5A polymorphisms and embryo survival was investigated for more than 1500 IVF embryos produced from 3 sires and 160 dams. The exonic SNP12195 is a silent mutation with a single nucleotide substitution of a G for a C in exon 8 of the STAT5A gene. Survival rate of embryos produced from sire 1 showed a highly significant association with seven SNPs including SNP12195. Similarly, five SNP showed significant association with survival rate of embryos produced from sire 2. For both sires, the directions of the effects were consistent for all significant SNP. However, for sire 3, a significant association with embryo survival rate was found for two SNP that showed the opposite effect to those found for sires 1 and 2. This is most likely due to linkage phase disequilibrium between those SNP markers and the causative mutation for early embryonic death.

Second, the association of fertilization rate of more than 2300 oocytes with STAT5A polymorphisms was evaluated. It is worth noting that the directions of the effects of two SNP (SNP3117 and SNP13244) were similar for the three sires, although for sire 2 the effects on fertilization rate did not reach the significance level. Although not willing to be bound by any theory, it is believed that this result could be explained by a direct effect of STAT5A mutations on fertilization success. However, the possibility exists that other SNPs in the gene or in genes nearby are responsible for the observed effects. The most significant associations with fertilization rate were for sire 3. However, STAT5A in this sire had less significant effects on embryo survival than sires 1 and 2. These observations indicate that the factors affecting embryo survival could differ from those affecting fertilization rate. Alternatively, the observed effects on embryo survival and fertilization rate could be associated with a common mutation in linkage disequilibrium with the examined polymorphisms.

Third, segregation ratio distortion was observed for embryos genotyped for SNP12195. One hypothesis for this distortion is the prezygote selection of sire gametes for fertilization. Indeed, for sire 3—heterozygous (GC) for SNP12195—the number of GG embryos produced from GG dams was much lower than expected and no GG embryos were produced from GC dams. Furthermore, a highly significant decrease in fertilization rate was observed for this sire. It remains to be determined whether or not the genotype of sires has any effect on the observed segregation distortion. Several studies have shown that sperm genotype is an important factor in female meiosis and can lead to unequal allele frequencies (Pardo-Manuel de Villena and Sapienza, 2001). The present invention showed significant segregation distortion for the two sires with genotype GC but not with the sire with genotype CC.

As indicated above, it is believed that most likely STAT5A has two mechanisms by which it affects embryo survival, although at present the relationship between these mechanisms is not clear. One is a prefertilization mechanism which involves sperm factors that cause low fertilization rate. This is supported by the results of sire 3 where almost no GG embryos were produced. The second is a postfertilization mechanism that causes incompatibility between the male pronucleus and the oocyte that in turn leads to embryo death before the blastocyst stage. Incompatibility between male and female gametes has been suggested as a mechanism leading to embryo death in mice (Wakasugi, 2007). In DDK syndrome, mating of females from the DDK inbred strain with males from other strains leads to arrest of cell division and proliferation and early embryonic death as a result of incompatibility between cytoplasmic factors of oocytes and spermatozoa factors (Wakasugi, 2007).

Genes causing embryonic death are difficult to identify. Nevertheless, two major genes affecting embryo survival have been detected in cattle: deficiency of uridine monophosphate synthase (DUMPS) and complex vertebral malformation (CVM). The deficient enzyme in DUMPS, uridine monophosphate synthase (UMP), is responsible for converting orotic acid to uridine monophosphate, which is an essential component of pyrimidine nucleotides. The homozygous condition for the defective, recessive allele of UMP results in embryonic death at about day 40 of pregnancy (omia.angis.org.au). Heterozygous×heterozygous matings require approximately 3.1 services per calving, compared to 2.0 for normal×normal matings. CVM is another lethal autosomal recessive disorder with onset during fetal development, leading to pregnancy loss and vertebral anomalies. Recently, it was shown that CVM is caused by a mutation in SLC35A3, which encodes an enzyme that transports nucleotide-sugars from the cytosol into the lumen of the endoplasmic reticulum and/or the Golgi apparatus (Thomsen et al., 2006). Bulls in the U.S. are tested for the lethal mutation and, at present, only 1% are carriers compared to 18% prior to 2001 (VanRaden and Miller, 2006).

These two genes are clearly distinct from STAT5A. First, DUMPS and CVM are relatively rare disorders, although they had a major impact in the dairy industry. Even at their highest prevalence in the Holstein population, the deleterious alleles were never represented in more than 20% of animals. In contrast, the present invention indicates that the embryonic lethal allele of the STAT5 gene is present in about 40% of the Holstein population. It also is present in other breeds of dairy cattle (unpublished data). Second, DUMPS and CVM cause pregnancy losses at later stages of pregnancy than the STAT5A, which appears to cause very early pregnancy loss. Surprisingly, the early nature of the STAT5A lethality may have slowed the identification of this mutation and may also have made it easier for this mutation to remain prevalent in the population. To illustrate, a pregnancy loss at 40-50 days would be readily identified by producers and would be extremely costly from both an economic and reproductive efficiency viewpoint. In contrast, an early embryonic loss would be regarded as a failure to conceive and the cow would be rebred in the next estrous cycle, and, if successful, would result in a shorter calving interval than if the pregnancy loss were at a later stage of gestation.

The present inventors chose STAT5A for association tests with milk production traits because of its role in mammary gland development. Brym et al. (2004) detected one SNP in intron 9 of STAT5A in association with milk production traits in 138 Jersey cows using single strand conformation polymorphism. In contrast, in the current study, SNP14217 in intron 9 did not show any significant association with milk production or health traits whereas allele G of SNP12195 was associated with a decrease in both protein and fat percentages and with a slight increase in SCS.

The STAT5A gene is a member of the signal transduction pathway of IFN-tau and PL. It is of interest that genes of this pathway are involved in both initiation of pregnancy of milk production and health traits. In previous studies, it has been shown that several genes in this pathway are associated with milk production and health traits (Leonard et al. 2005; Cobanoglu et al., 2006; Khatib et al., 2007a; Khatib et al., 2007b). Thus, this pathway represents a unique system to investigate the complex relationship between milk production and pregnancy of cows at the molecular level. In this study, polymorphisms of STAT5A were found to be associated with both milk composition and infertility although the relationship between these two phenotypes remains contentious. Washburn et al. (2002) analyzed the relationship of conception rate and milk production over more than a 20-year time period (1976-1999) in dairy herds in the Southeastern U.S. It was clear that conception rates decreased from about 55% to about 35% during this time period as milk production dramatically increased. Faust et al. (1988) showed a clear negative relationship between level of milk production and conception rate in primiparous Holstein dairy cattle. In contrast, Peters and Pursley (2002) reported that higher-producing cows had greater conception rates following a hormone injection series to synchronize estrus than lower-producing cows.

STAT5A is the first gene found to affect both milk production and fertility. It is important to note that the G allele of SNP12195 was associated with a significant decrease in milk protein and fat percentages and with low embryo survival, making this SNP an attractive candidate for marker assisted selection in dairy cattle. Moreover, it would be of great interest to investigate the effects of additional genes in the signal transduction pathway of IFN-tau and PL in order to shed more light on the complex nature of the relationship between pregnancy and milk production.

The following examples are intended to illustrate preferred embodiments of the invention and should not be interpreted to limit the scope of the invention as defined in the claims.

EXAMPLES

Materials and Methods

Polymorphism Identification

Genomic DNA was extracted from bovine ovaries by grinding 30-100 mg from each ovary using the AquaPure Genomic DNA kit (Bio-Rad, Hercules, Calif.). In order to detect single nucleotide polymorphisms (SNPs) in the STAT5A gene (GenBank accession number NC_007317), DNA pools were constructed from 50 different ovary samples and amplified with the primers listed in Table 1. Primers were designed in STAT5A to amplify fairly regularly-spaced exonic and intronic regions of the gene, with the exception of a 2619 bp stretch extending from intron 5 to intron 7. In this region, the STAT5A and STAT5B genes share about 99.43% of their sequence, making it nearly impossible to design STAT5A-specific primers. The PCR products of the pooled DNA samples were sequenced using BigDye terminator (Applied Biosystems, Foster City, Calif.), and SNPs were identified by visually inspecting sequence traces. For individual genotyping, ovary DNA was sequenced.

In Vitro Fertilization and Survival Rate Assessment

Ovaries were collected from a total of 160 Holstein cows obtained from a local abattoir in Wisconsin. Oocytes were aspirated from antral follicles (>2-6 mm) and selected for study if a compact cumulus of several cell layers was present. Oocytes were processed in TALP-Hepes with 0.22 mM sodium pyruvate, 25 µg/ml gentamicin sulfate, and 3 mg/ml BSA. Oocytes were incubated for 20-24 hours in 50 ul drops of maturation medium that had been equilibrated in 5% carbon dioxide in air at 39° C. and high humidity. Maturation medium consisted of M199 with Earle's salts supplemented with bovine LH and FSH (3 ug/ml each) from Sioux Biochemical (Sioux center, Iowa, 51250), 0.22 mM sodium pyruvate, 25 µg/ml gentamicin sulfate and 10% fetal bovine serum. After 20-24 hours of maturation, oocytes were washed 3× in TALP-Hepes and placed up to 10 oocytes per 44 ul mineral oil overlaid microdrop of IVF-Talp (Biowhittaker, Walkersburg, Md.) supplemented with 0.22 mM sodium pyruvate, 25 µg/ml gentamicin sulfate, and 6 mg/ml essentially fatty acid free BSA.

Oocytes were fertilized with frozen-thawed; percoll separated bull semen after being adjusted to a final concentration of 1 million sperm/ml. Each microdrop received 2.0 ug/ml heparin to help induce capacitation as well as hypotaurine, penicillamine, and epinephrine to maintain sperm membrane integrity and motility. Oocytes and sperm were co-incubated for a period of 18-24 hours. After the fertilization period, putative zygotes were stripped of their cumulus cells by vortexing for 3 minutes and washed 3× in TALP-Hepes before being placed into 50 ul mineral oil overlaid microdrops of synthetic oviductal fluid (Biowhittaker) supplemented with 0.22 mM sodium pyruvate, 25 µg/ml gentamicin sulfate, and 8 mg/ml essentially fatty acid free BSA.

Survival rate of embryos (number of viable embryos out of total cultured) was evaluated at day 7 of development (fertilization=day 0). Embryos were preserved in RNALater RNA Stabilization reagent (Qiagen, Valencia, Calif.) to avoid RNA degradation. The proportion of unfertilized ova (UFO) was calculated as the number of unsuccessful fertilizations out of the total embryos cultured.

SNP Association Testing with Fertilization and Embryonic Survival Rates

The association between the SNP and fertilization and embryonic survival rates were studied using a generalized linear model methodology (McCullagh and Nelder, 1989) for proportion data, using the binomial distribution and the logit link function. First, a between-sire analysis was considered, with a model (linear predictor) including the effects of sire, genotype of the dam, as well as their interaction. Due to consistent significance of the effects of sire and sire by dam genotype interaction, a series of within-sire analyses was performed for each SNP. The results are expressed in terms of test statistics (chi-square) values and associated p-values, as well as proportion (fertilization and survival rates) confidence intervals for each genotypic group of dams mated with each sire. These analyses were performed using the GENMOD procedure of SAS (SAS Institute, 2006).

Embryo Genotyping

Genomic DNA was extracted from single, day 7 embryos using Ambion kit (Applied Biosystems, Foster City, Calif.). Embryos were genotyped for SNP12195 (G/C) in exon 8 of STAT5A using primers STATF1 and STATR1 (Table 1). Amplification was performed in a 25 µl reaction volume, which included 3 µl of embryo DNA, 50 ng each primer, 200 µM each dNTP, 5.0 µl 5×PCR buffer (Promega, Madison, Wis.), and 1.5 u Taq DNA polymerase (Promega). The temperature cycles were as follows: 95° C. for 5 min, followed by 32 cycles of 94° C. for 45 s, touchdown annealing from 65-53° C. for 45 s, 72° C. for 45 s, and a final extension at 72° C. for 7 min. The PCR products were amplified in a nested PCR reaction using primers STAT14 and STAT13 (Table 1). The nested PCR reaction included 1 µl PCR product, 50 ng each primer, 200 µM each dNTP, 5.0 µl 5×PCR buffer, and 1.5 u Taq DNA polymerase (Promega). The temperature cycles were as described for the first PCR except the total number of cycles which was set to 18. Products of the nested PCR were genotyped by sequencing and also digestion with the restriction enzyme BstEII, which distinguishes alleles C and G of SNP12195.

TABLE 1

Primer sequences, locations, and amplification product sizes

| Primer | location | sequence | Product size (bp) |
|---|---|---|---|
| AF1 (SEQ ID NO: 3) | Intron 1 | GAGAGAGGGAGTGTCTTGTCTC | 831 |
| AR1 (SEQ ID NO: 4) | Intron 2 | GACTCCCATTTCCCTGTTCC | |
| AF2 (SEQ ID NO: 5) | Intron 2 | GGAACAGGGAAATGGGAGTC | 779 |
| AR2 (SEQ ID NO: 6) | Intron 3 | CCTTCCTCCCACACCCTCAC | |
| AF3 (SEQ ID NO: 7) | Intron 3 | GTGAGGGTGTGGGAGGAAGG | 889 |
| AR3 (SEQ ID NO: 8) | Intron 4 | CACACACACTTGCCTGTGTG | |
| AF4 (SEQ ID NO: 9) | Intron 4 | CACACAGGCAAGTGTGAGAG | 881 |
| AR4 (SEQ ID NO: 10) | Intron 4 | GATATCAGTGTCCACCACAAG | |
| AF5 (SEQ ID NO: 11) | Intron 4 | CTTGTGGTGGACACTGATATC | 586 |
| AR5 (SEQ ID NO: 12) | Intron 4 | ACCCTCTGTGACCTGGCAAC | |
| AF6 (SEQ ID NO: 13) | Intron 4 | GAAGCCAGGTCACAGAGGGT | 641 |
| AR6 (SEQ ID NO: 14) | Intron 4 | GAAGCCAGGTCACAGAGGGT | |
| AF7 (SEQ ID NO: 15) | Intron 4 | GCCCAGTGCTTAAGAATCTG | 631 |
| AR7 (SEQ ID NO: 16) | Intron 4 | GGCAGACTCTGGTAGAAACTTC | |

TABLE 1-continued

Primer sequences, locations, and amplification product sizes

| Primer | location | sequence | Product size (bp) |
|---|---|---|---|
| AF8 (SEQ ID NO: 17) | Intron 4 | GAAGTTTCTACCAGAGTCTGCC | 832 |
| AR8 (SEQ ID NO: 18) | Intron 5 | CCCAGGCCAAATTGCATGTTC | |
| AF9 (SEQ ID NO: 19) | Intron 5 | GAACATGCAATTTGGCCTGGG | 859 |
| AR9 (SEQ ID NO: 20) | Intron 5 | CATCAAGATAGAGCACATGCC | |
| AF10 (SEQ ID NO: 21) | Intron 5 | GGCATGTGCTCTATCTTGATG | 549 |
| AR10 (SEQ ID NO: 22) | Intron 5 | GCTACCTCTCTATCTATAGGAGC | |
| AF11 (SEQ ID NO: 23) | Intron 9 | AGCCTCTGCTCTGTAGCTGG | 649 |
| AR11 (SEQ ID NO: 24) | Intron 9 | TCTTGTTCCCAGCCCAAAGG | |
| AF12 (SEQ ID NO: 25) | Intron 9 | CCTTTGGGCTGGGAACAAGA | 649 |
| AR12 (SEQ ID NO: 26) | Intron 9 | ATCAACCTGAGAGCATCCGAG | |
| AF13 (SEQ ID NO: 27) | Intron 9 | CTCGGATGCTCTCAGGTTGAT | 971 |
| AR13 (SEQ ID NO: 28) | Intron 11 | GCCATTCCACAAGCCCCTTC | |
| AF14 (SEQ ID NO: 29) | Intron 11 | GAAGGGGCTTGAGGAATGGC | 889 |
| AR14 (SEQ ID NO: 30) | Intron 13 | AGGGGTAGAGATAGTCCCAG | |
| AF15 (SEQ ID NO: 31) | Intron 13 | CTGGGACTATCTCTACCCCT | 659 |
| AR15 (SEQ ID NO: 32) | Intron 13 | GTTAGGGCTTGTGTCCCCATC | |
| AF16 (SEQ ID NO: 33) | Intron 13 | GATGGGGACACAAGCCCTAAC | 730 |
| AR16 (SEQ ID NO: 34) | Intron 15 | GAGGATTGGAGCTGTAGGGC | |
| AF17 (SEQ ID NO: 35) | Intron 15 | GCCCTACAGCTCCAATCCTC | 809 |
| AR17 (SEQ ID NO: 36) | Intron 16 | CACCTGCTGACAGTCACCAG | |
| AF18 (SEQ ID NO: 37) | Exon 17 | GCAAGTGGTCCCGCAGTAAG | 737 |
| AR18 (SEQ ID NO: 38) | Intron 18 | CAGTCCCATGTGGTAGGTAC | |
| AF19 (SEQ ID NO: 39) | Intron 18 | GTACCTACCACATGGGACTG | 980 |
| AR19 (SEQ ID NO: 40) | Exon 19 | CATGTGTACATGGGCTGCCTG | |
| STATF1 (SEQ ID NO: 41) | Exon 8 | GAGAAGTTGGCGGAGATTATC | 840 |
| STATR1 (SEQ ID NO: 42) | Intron 9 | CCGTGTGTCCTCATCACCTG | |
| STAT14 (SEQ ID NO: 43) | Exon 8 | GAGGAGATGCTGGCTGAGGT | 440 |
| STAT13 (SEQ ID NO: 44) | Intron 8 | TTCAGGGGACAGGACTCTGG | |

Milk Production Data and Cow Population Genotyping

Blood samples were obtained from the University of Wisconsin daughter design resource population (henceforth: UW resource population). This population was originally created to search for quantitative trait loci (QTL) in association with susceptibility to paratuberculosis. For a detailed description of this population see Gonda et al. (2006) and Cobanoglu et al. (2006). Yield deviation (YD) and predicted transmitting abilities (PTA) data for daughters in the UW resource populations were obtained for milk, protein, and fat yields (kg), protein and fat percentages, and somatic cell score (SCS) from the USDA Animal Improvement Programs Laboratory (Beltsville, Md.).

Genomic DNA was extracted from blood samples using GFX Genomic Blood DNA Purification Kit (Amersham Biosciences, Piscataway, N.J.). All samples were genotyped for SNP12195 (exon 8) and SNP14217 (intron 9). SNP12195 (G/C) was genotyped using primers STATF1 and STATR1 (Table 1). Amplification was performed in a 25 µl reaction volume, which included 25-50 ng genomic DNA, 50 ng each primer, 200 µM each dNTP, 5.0 µl 5×PCR buffer (Promega), and 1.5 u Taq DNA polymerase (Promega). The temperature cycles were as follows: 95° C. for 5 min, followed by 32 cycles of 94° C. for 45 s, touchdown annealing from 65-53° C. for 45 s, 72° C. for 45 s, and a final extension at 72° C. for 7 min. SNP14217 (A/G) was genotyped by GeneSeek Inc. (Lincoln, Nebr.).

SNP Association Testing with Milk Production Traits

Yield deviation data for each trait were analyzed using the following model:

$$YD_{ijk} = \mu + s_i + d_{ij}\tau + g_k + \epsilon_{ijk},$$

where $YD_{ijk}$ represents the observation relative to daughter j of sire i; $\mu$ is a general constant (intercept); $s_i$ is the fixed effect of sire i; $\tau$ is an effect associated with *M. paratuberculosis* infection status, $d_{ij}$ is an disease indicator variable assuming the values 0 and 1 for non-infected and infected cows, respectively; $g_k$ is the effect of the genotypic group k; and $\epsilon_{ij}$ is a residual term. Specific contrasts of interest were used to estimate and to test for additive and dominance genetic effects as described in as in Khatib et al. (2007a).

In addition, PTA values of the cows were studied using an allele substitution model expressed as:

$$PTA_{ij} = \mu + s_i + \beta x_k + \epsilon_{ijk},$$

where $PTA_{ij}$ is the observation relative to daughter j of sire i; $s_i$ and $\epsilon_{ijk}$ are defined as before; $\beta$ is the regression coefficient representing half of the allele substitution effect ($\alpha/2$), and $x_k$ is the number of copies (0, 1 or 2) of the less frequent allele at the marker locus on daughter j of sire i. All analyses were implemented using the GLM procedure of SAS (SAS Institute, 2006).

Results

Example 1

Identified Polymorphisms

Search for single nucleotide polymorphisms in 15,291 bp of genomic STAT5A revealed a total of 12 SNPs in which 11 SNPs were identified in introns and one SNP (SNP12195) was identified in exon 8. SNP3117, SNP3419, and SNP3470 were identified in intron 4. SNP12885, SNP12924, SNP13244, SNP13319, SNP13516, SNP13654, and SNP14217 were identified in intron 9. SNP15541 was identified in intron 12. All cows used in the in vitro fertilization (IVF) experiment were individually genotyped for the 12 SNPs by sequencing.

Example 2

Embryo Survival and Fertilization Rates

A total of 1551 embryos were produced by IVF, and survival rate was measured at day 7 of development. Table 2 shows the survival rates of embryos and genotypes of cows and sires for the 12 SNPs. For SNP3419, SNP13319, SNP13654, and SNP15541, a small number of one of the homozygous genotypes was observed, therefore these SNPs were not further analyzed for the association with survival and fertilization rates. FIG. 2A shows the chi-square results for the survival rate of embryos produced from the three sires. For sire 1, seven SNP (SNP3117, SNP12195, SNP12885, SNP12924, SNP13244, SNP13516, and SNP14217) showed a highly significant association (P<0.0001) with embryo survival rate. For example, for SNP3117, the survival rate of embryos produced from the mating of sire 1 (A/G) and genotype GG dams, was 46% vs. 21% and 28%, for embryos produced from AG and AA dams, respectively (Table 2). For sire 2, SNP3117, SNP12885, SNP12924, SNP13244, and SNP14217 showed significant association with survival rate. In contrast, for sire 3, only two SNP (SNP3117 and SNP13244) showed significant association with embryo survival rate.

TABLE 2

Embryo survival and UFO ratios and genotypes of cows and sires for the 12 SNP in the STAT5A gene

| SNP/sire | sire geno-type | dams' genotypes | embryo survival rate | total embryos | UFO ratio | total embryos and UFOs |
|---|---|---|---|---|---|---|
| SNP3117 | | | | | | |
| Sire 1 | AG | AA | 0.28 | 188 | 0.41 | 317 |
| | | AG | 0.21 | 95 | 0.38 | 152 |
| | | GG | 0.46 | 200 | 0.30 | 285 |
| Sire 2 | GG | AA | 0.42 | 124 | 0.35 | 192 |
| | | AG | 0.27 | 139 | 0.37 | 219 |
| | | GG | 0.43 | 75 | 0.31 | 109 |
| Sire 3 | GG | AA | 0.37 | 188 | 0.36 | 293 |
| | | AG | 0.42 | 281 | 0.30 | 399 |
| | | GG | 0.32 | 248 | 0.20 | 309 |
| SNP3419 | | | | | | |
| Sire 1 | CT | CC | 0.24 | 59 | 0.39 | 423 |
| | | CT | 0.39 | 134 | 0.35 | 206 |
| | | TT | 0 | 0 | | 0 |
| Sire 2 | TT | CC | 0.38 | 165 | 0.36 | 257 |
| | | CT | 0.34 | 167 | 0.35 | 257 |
| | | TT | 0.46 | 13 | 0.24 | 17 |
| Sire3 | TT | CC | 0.42 | 315 | 0.34 | 478 |
| | | CT | 0.35 | 384 | 0.21 | 485 |
| | | TT | 0.24 | 33 | 0.39 | 54 |
| SNP3470 | | | | | | |
| Sire 1 | AG | AA | 0.25 | 198 | 0.41 | 335 |
| | | AG | 0.31 | 139 | 0.33 | 207 |
| | | GG | 0.41 | 56 | 0.36 | 87 |
| Sire 2 | GG | AA | 0.40 | 131 | 0.35 | 203 |
| | | AG | 0.31 | 167 | 0.38 | 269 |
| | | GG | 0.45 | 47 | 0.20 | 59 |
| Sire 3 | GG | AA | 0.39 | 248 | 0.36 | 388 |
| | | AG | 0.38 | 435 | 0.21 | 554 |
| | | GG | 0.27 | 49 | 0.35 | 75 |
| SNP12195 | | | | | | |
| Sire 1 | GC | CC | 0.52 | 144 | 0.3 | 207 |
| | | GC | 0.22 | 224 | 0.39 | 368 |
| | | GG | 0.29 | 136 | 0.39 | 223 |
| Sire 2 | CC | CC | 0.44 | 96 | 0.31 | 140 |
| | | GC | 0.33 | 138 | 0.34 | 208 |
| | | GG | 0.34 | 96 | 0.43 | 168 |
| Sire 3 | GC | CC | 0.36 | 147 | 0.33 | 218 |
| | | GC | 0.41 | 333 | 0.30 | 474 |
| | | GG | 0.39 | 133 | 0.35 | 206 |
| SNP12885 | | | | | | |
| Sire 1 | AC | AA | 0.34 | 140 | 0.32 | 205 |
| | | AC | 0.19 | 170 | 0.41 | 287 |
| | | CC | 0.55 | 91 | 0.28 | 127 |
| Sire 2 | CC | AA | 0.41 | 93 | 0.42 | 161 |
| | | AC | 0.25 | 92 | 0.25 | 123 |
| | | CC | 0.39 | 83 | 0.31 | 121 |
| Sire 3 | CC | AA | 0.43 | 240 | 0.33 | 359 |
| | | AC | 0.36 | 165 | 0.26 | 223 |
| | | CC | 0.36 | 147 | 0.30 | 210 |
| SNP12924 | | | | | | |
| Sire1 | CT | CC | 0.55 | 91 | 0.28 | 127 |
| | | CT | 0.19 | 170 | 0.41 | 287 |
| | | TT | 0.34 | 140 | 0.32 | 205 |
| Sire 2 | CC | CC | 0.40 | 94 | 0.31 | 135 |
| | | CT | 0.26 | 142 | 0.33 | 213 |
| | | TT | 0.41 | 75 | 0.38 | 121 |
| Sire 3 | CC | CC | 0.35 | 142 | 0.29 | 199 |
| | | CT | 0.41 | 239 | 0.31 | 346 |
| | | TT | 0.45 | 195 | 0.33 | 289 |
| SNP13244 | | | | | | |
| Sire 1 | AG | AA | 0.33 | 152 | 0.35 | 234 |
| | | AG | 0.19 | 170 | 0.41 | 287 |
| | | GG | 0.55 | 91 | 0.28 | 127 |
| Sire 2 | GG | AA | 0.43 | 87 | 0.41 | 147 |
| | | AG | 0.26 | 142 | 0.33 | 213 |
| | | GG | 0.40 | 105.00 | 0.31 | 153 |
| Sire 3 | GG | AA | 0.39 | 187 | 0.31 | 272 |
| | | AG | 0.43 | 260 | 0.30 | 272 |
| | | GG | 0.30 | 276.00 | 0.21 | 351 |

TABLE 2-continued

Embryo survival and UFO ratios and genotypes of cows and sires for the 12 SNP in the STAT5A gene

| SNP/sire | sire genotype | dams' genotypes | embryo survival rate | total embryos | UFO ratio | total embryos and UFOs |
|---|---|---|---|---|---|---|
| SNP13319 | | | | | | |
| Sire 1 | GG | AA | 0.61 | 31 | 0.18 | 38 |
| | | AG | 0.35 | 54 | 0.36 | 85 |
| | | GG | 0.29 | 328 | 0.38 | 525 |
| Sire 2 | GG | AA | 0 | 0 | 0 | 0 |
| | | AG | 0.23 | 52 | 0.30 | 74 |
| | | GG | 0.37 | 282 | 0.36 | 439 |
| Sire 3 | GG | AA | 0.60 | 10 | 0.33 | 15 |
| | | AG | 0.32 | 219 | 0.23 | 284 |
| | | GG | 0.40 | 482 | 0.30 | 684 |
| SNP13516 | | | | | | |
| Sire 1 | GT | GG | 0.53 | 143 | 0.29 | 200 |
| | | GT | 0.22 | 208 | 0.40 | 345 |
| | | TT | 0.30 | 142.00 | 0.35 | 220 |
| Sire 2 | GG | GG | 0.40 | 105.00 | 0.31 | 135 |
| | | GT | 0.29 | 132 | 0.33 | 197 |
| | | TT | 0.36 | 91 | 0.43 | 160 |
| Sire 3 | GG | GG | 0.37 | 127 | 0.31 | 184 |
| | | GT | 0.42 | 271 | 0.31 | 395 |
| | | TT | 0.36 | 270 | 0.21 | 342 |
| SNP13654 | | | | | | |
| Sire 1 | AA | AA | 0.29 | 371 | 0.38 | 594 |
| | | AG | 0.41 | 113 | 0.31 | 163 |
| | | GG | 0.83 | 18 | 0.22 | 23 |
| Sire 2 | AA | AA | 0.38 | 297 | 0.36 | 461 |
| | | AG | 0.25 | 48 | 0.30 | 69 |
| | | GG | 0 | 0 | 0 | 0 |
| Sire 3 | AA | AA | 0.40 | 489.00 | 0.29 | 692 |
| | | AG | 0.31 | 197 | 0.22 | 254 |
| | | GG | 0.60 | 10.00 | 0.33 | 15 |
| SNP14217 | | | | | | |
| Sire 1 | AG | AA | 0.31 | 149 | 0.39 | 243 |
| | | AG | 0.22 | 234 | 0.38 | 377 |
| | | GG | 0.55 | 131 | 0.30 | 188 |
| Sire 2 | GG | AA | 0.39 | 83 | 0.42 | 144 |
| | | AG | 0.24 | 118 | 0.36 | 184 |
| | | GG | 0.41 | 85 | 0.35 | 130 |
| Sire 3 | GG | AA | 0.38 | 175 | 0.30 | 249 |
| | | AG | 0.41 | 272 | 0.30 | 389 |
| | | GG | 0.32 | 179 | 0.25 | 238 |
| SNP15541 | | | | | | |
| Sire 1 | CC | CC | 0.28 | 395 | 0.36 | 614 |
| | | CT | 0.54 | 74 | 0.29 | 104 |
| | | TT | 0.83 | 18 | 0.22 | 23 |
| Sire 2 | CC | CC | 0.36 | 280 | 0.37 | 441 |
| | | CT | 0.23 | 52 | 0.30 | 74 |
| | | TT | 0 | 0 | 0 | 0 |
| Sire 3 | CC | CC | 0.40 | 490.00 | 0.29 | 693 |
| | | CT | 0.32 | 207 | 0.23 | 268 |
| | | TT | 0.60 | 10.00 | 0.33 | 15 |

FIG. 2B shows the chi-square results of UFO for the eight SNP analyzed for the three sires. For sire 1, the rate of UFO was significantly associated (P<0.05) with SNP3117, SNP12885, SNP12885, SNP12924, SNP13244, SNP13516. The UFO ratio for genotype AA dams was 41% vs. 30% for genotype GG of SNP3117 (Table 2). Similarly, for SNP12924, UFO ratio was 41% for CT genotype vs. 28% for CC genotype (Table 2). Also, genotypes of the exonic SNP12195 showed slight differences for UFO (P=0.081). For sire 2, significant associations with UFO were found for SNP3470 (P<0.05) and SNP12885 (P<0.01). For SNP12885, UFO ratio for the AA genotype was 42% vs. 25% for the AC genotype (Table 2). For sire 3, a highly significant association with UFO was observed for SNP3117 and SNP3470 (P<0.0001, for both SNP).

Example 3

Segregation Distortion of STAT5A Genotypes

Table 3 shows genotypes of embryos and the parents for exonic SNP12195. To determine if there were genotype differences in pre-blastocyst stage embryonic losses, 145 of the surviving embryos were genotyped. For sire 1 (GC), when coupled with CC dams, of the surviving embryos, ten had the CC genotype and four had GC.

Genotyping of embryos produced from Sire 1 and GG dams revealed a significant excess of GG vs. GC embryos (P=0.011). For sire 3 (GC), a significant segregation distortion was observed for all pairings (Table 3). Of particular interest was the observation of the decreased number of embryos with the GG genotype. Only two surviving GG embryos were produced from sire 3 and GG dams vs. 14 GC embryos (P=0.002). Similarly, no GG genotypes were detected from the pairing of sire 3 with GC dams (P=0.001). The coupling of sire 3 with CC dams resulted in an excess of CC vs. GC embryos (P=0.019). Sire 2 was homozygous (CC) for this SNP.

TABLE 3

SNP12195 genotypes of embryos produced from sires 1, 2, and 3

| Sire | sire genotype | dams' genotypes | embryo genotype CC | embryo genotype GC | embryo genotype GG | P value |
|---|---|---|---|---|---|---|
| #1 | GC | CC | 10 | 4 | — | 0.108 |
| #1 | | GG | — | 4 | 15 | 0.011 |
| #1 | | GC | 1 | 2 | 2 | |
| #2 | CC | CC | 23 | — | — | |
| #2 | | GG | — | 7 | — | |
| #2 | | GC | 11 | 15 | — | 0.432 |
| #3 | GC | CC | 8 | 1 | — | 0.019 |
| #3 | | GG | — | 14 | 2 | 0.002 |
| #3 | | GC | 13 | 13 | 0 | 0.001 |

Example 4

Association with Milk Production Traits

Genotyping results of 887 cows from the UW resource population revealed that the frequency of the C and G alleles at SNP12195 were 0.61 and 0.39, respectively. Similarly, frequencies of the A and G alleles at SNP14217 were 0.39 and 0.61, respectively. Table 4 shows that allele G of SNP12195 was associated with a significant decrease in fat and protein percentages and with a less significant decrease in somatic cell score. In contrast, SNP14217 was not significant for any of the examined traits. Estimates of dominant and additive effects of SNP12195 revealed that the GG genotype of this SNP was associated with a significant decrease in protein percentage and a decrease in fat percentage (Table 5). SNP14217 did not show significant association with any of the examined traits (Table 5).

TABLE 4

Estimates of the allele substitution effect of SNP14217 and SNP12195 and standard errors (SE) for production traits in the UW resource population

| Trait | SNP14217 Estimate ± SE | SNP12195 Estimate ± SE |
|---|---|---|
| Fat yield (kg) | 1.80 ± 2.34 | −1.75 ± 2.48 |
| Fat % | −0.0031 ± 0.0084 | −0.0186 ± 0.0090* |
| Milk yield (kg) | 69.1 ± 60.9 | 82.8 ± 64.6 |
| Protein yield (kg) | 1.20 ± 1.64 | 0.01 ± 1.74 |
| Protein % | −0.0035 ± 0.0040 | −0.0101 ± 0.0042* |
| SCS (points) | 0.0190 ± 0.0124 | 0.0226 ± 0.0130† |

†P < 0.10
*P < 0.05

TABLE 5

Estimates (±SE) of the additive and dominance effects associated with SNP12195 in the UW resource population

| Trait | Additive effect | Dominance effect | P value |
|---|---|---|---|
| Fat yield | −2.07 ± 4.84 | 2.41 ± 5.23 | 0.8658 |
| Fat %† | −0.031 ± 0.017† | −0.013 ± 0.019 | 0.0641 |
| Milk yield | 161.7 ± 129.1 | 144.2 ± 139.5 | 0.1225 |
| Protein yield | 1.15 ± 3.45 | 2.48 ± 3.72 | 0.6547 |
| Protein %** | −0.018 ± 0.008* | −0.009 ± 0.008 | 0.0098 |
| SCS | 0.095 ± 0.073 | −0.038 ± 0.079 | 0.4320 |

†P < 0.10
*P < 0.05
**P < 0.01

REFERENCES

Brym, P., S. Kaminski and A. Rusc. 2004. New SSCP polymorphism within bovine STAT5A gene and its associations with milk performance traits in Black-and-White and Jersey cattle. J. Appl. Genet. 45:445-452.

Chen, X., U. Vinkemeier, Y. Zhao, D. Jeruzalmi, J. E. Darnell and j. Kuriyan. 1998. Crystal structure of a tyrosine phosphorylated STAT-1 dimer bound to DNA. Cell 93:827-839.

Cobanoglu, O., I. Zaitoun, Y. M. Chang, G. E. Shook, and H. Khatib. 2006. Effects of the signal transducer and activator of transcription 1 (STAT1) gene on milk production traits in Holstein dairy cattle. J. Dairy Sci. 89:4433-4437.

Darnell, J. E. 1997. STATs and gene regulation. Science 277:1630-1635.

Faust, M. A., B. T. McDaniel, O. W. Robison and J. H. Britt. 1988. Environmental and yield effects on reproduction in primiparous Holsteins. J. Dairy Sci. 71:3092-3099.

Gonda, M. G., Y. M. Chang, G. E. Shook, M. T. Collins and B. W. Kirkpatrick. 2006. Genetic variation of *Mycobacterium avium* ssp. paratuberculosis infection in US Holsteins. J. Dairy Sci. 89:1804-1812.

Khatib, H., V. Schutzkus, Y. M. Chang and G. J. M. Rosa. 2007a. Pattern of expression of the uterine milk protein gene and its association with productive life in dairy cattle. J. Dairy Sci. 90:2427-2433.

Khatib, H., I. Zaitoun, J. Wiebelhaus-Finger, Y. M. Chang and G. J. M. Rosa. 2007b. The association of bovine PPARGC1A and OPN genes with milk composition in two independent Holstein cattle populations. J. Dairy Sci. 90:2966-2970.

Kisseleva, T., S. Bhattacharya, J. Braunstein and C. W. Schindler. 2002. Signaling through the JAK/STAT pathway, recent advances and future challenges. Gene 285:1-24.

Leonard, S., H. Khatib, V. Schutzkus, Y. M. Chang, and C. Maltecca. 2005. Effects of the osteopontin gene variants on milk production traits in dairy cattle. J. Dairy Sci. 88:4083-4086.

McCullagh, P. and J. A. Nelder. 1989. Generalized Linear Models. 2nd ed. London: Chapman and Hall.

Miyoshi, K., J. M. Shillingford, G. H. Smith, S. L. Grimm, K. U. Wagner, T. Oka, J. M. Rosen, G. W. Robinson and L. Hennighausen. Signal transducer and activator of transcription (Stat) 5 controls the proliferation and differentiation of mammary alveolar epithelium. J. Cell Biol. 155: 531-542.

Pardo-Manuel de Villena, F. and C. Sapienza. 2001. Nonrandom segregation during meiosis: the unfairness of females. Mamm. Genome 12:331-339.

Peters, M. W. and J. R. Pursley. 2002. Fertility of lactating dairy cows treated with Ovsynch after presynchronization injections of PGF2☐ and GnRH. J. Dairy Sci 85:2403-2406.

SAS Institute. 2006. SAS OnlineDoc, Version 9.1. SAS Institute Inc., Cary, N.C.

Spencer, T. E. and F. W. Bazer. 2002. Biology of progesterone action during pregnancy recognition and maintenance of pregnancy. Front. Biosci. 1:d1879-1898.

Spencer, T. E. and F. W. Bazer. 2004. Conceptus signals for establishment and maintenance of pregnancy. Reprod. Biol Endocrinol. 2:49.

Stewart, M. D., Y. Choi, G. A. Johnson, L. Y. Yu-Lee, F. W. Bazer and T. E. Spencer. 2002. Roles of Stat1, Stat2, and interferon regulatory factor-9 (IRF-9) in interferon tau regulation of IRF-1. Biol. Reprod. 66:393-400.

Teglund, S., C. McKay, E. Schuetz, J. M. van Deursen, D. Stravopodis, D. Wang, M. Brown, S. Bodner, G. Grosveld and J. N. Ihle. 1998. Stat5a and Stat5b proteins have essential and nonessential, or redundant, roles in cytokine responses. Cell 93:841-850.

Thomsen, B., P. Horn, F. Panitz, E. Bendixen, A. H. Petersen, L. E. Holm, V. H. Nielsen, J. S. Agerholm, J. Ambjerg and C. Bendixen. 2006. A missense mutation in the bovine SLC35A3 gene, encoding a UDP-N-acetylglucosamine transporter, causes complex vertebral malformation. Genome Res. 16:97-105.

VanRaden, P. M. and R. H. Miller. 2006. Effects of nonadditive genetic interactions, inbreeding, and recessive defects on embryo and fetal loss by seventy days. J. Dairy Sci. 89:2716-2721.

Washburn, S. P., W. J. Silvia, C. H. Brown, B. T. McDaniel and A. J. McAllister. 2002. Trends in reproductive performance in southeastern Holstein and Jersey DHI herds. J. Dairy Sci 85:244-251.

Wakasugi, N. 2007. Embryologic, cytobiologic and genetic interpretations of DDK syndrome in mice. Dev. Growth Differ. 49:555-559.

Watson, C. J. 2001. Stat transcription factors in mammary gland development and tumorigenesis. J. Mammary Gland Biol. Neoplasia 6:115-127.

What is claimed is:

1. A dairy cattle breeding method for desirable fertilization rate or embryo survival rate, or both, the method comprising determining the identity of a nucleotide of the STAT5A gene of a dairy cattle cell or tissue corresponding to at least one position selected from the group consisting of position 3117, position 13244, position 13319, and position 13516 of SEQ ID NO: 1, and using a cell or tissue for breeding purposes only if said cell or tissue has at least one polymorphism selected from the group consisting of guanine at position 3117, a guanine at position 13244, an adenine base at position 13319, and guanine at position 13516 of the STAT5A gene.

2. A method according to claim 1, wherein the dairy cattle cell is an adult cell, an embryo cell, a sperm, an egg, a fertilized egg, or a zygote.

3. A method according to claim 1, wherein the identity of the nucleotide is determined by sequencing the STAT5A gene, or a fragment thereof comprising at least one position selected from the group consisting of position 3117, position 13244, position 13319, and position 13516 of SEQ ID NO: 1, isolated from the cell or tissue.

4. A method according to claim 3, wherein the STAT5A gene or fragment thereof is isolated from the cell or tissue via amplification by the polymerase chain reaction (PCR) of genomic DNA of the cell or tissue, or by RT-PCR of the mRNA of the cell or tissue.

5. A method according to claim 3, wherein the identity of both copies of the STAT5A gene is determined.

6. A method for selectively breeding of cattle, the method comprising superovulating a female animal, collecting eggs from said superovulated female, in vitro fertilizing said eggs from a suitable male animal, culturing said fertilized eggs into developing embryos, determining the identity of a nucleotide of the STAT5A gene of a developing embryo corresponding to at least one position selected from the group consisting of position 3117, position 13244, position 13319, and position 13516 of SEQ ID NO: 1, and planting developing embryo into a suitable female only if the STAT5A gene of the developing embryo has at least one polymorphism selected from the group consisting of guanine at position 3117, a guanine at position 13244, an adenine base at position 13319, and guanine at position 13516 of the STAT5A gene.

7. The method according to claim 6, wherein a developing embryo is planted into a suitable female only if the STAT5A gene of the developing embryo also has cytosine at a position corresponding to position 12195 of SEQ ID NO: 1.

8. The method of claim 6, wherein a developing embryo is planted into a suitable female only if the STAT5A gene of the developing embryo has guanine at a position corresponding to position 3117 of SEQ ID NO: 1, cytosine at a position corresponding to position 12195 of SEQ ID NO: 1, a guanine at a position corresponding to position 13244 of SEQ ID NO: 1, an adenine base at a position corresponding to position 13319 of SEQ ID NO: 1, and guanine at a position corresponding to position 13516 of SEQ ID NO: 1.

9. A method for selectively breeding dairy cattle for improved fertilization rate, comprising selecting a bull whose STAT5A gene is homozygously guanine at a position corresponding to position 3117 of SEQ ID NO: 1, guanine at a position corresponding to position 13244 of SEQ ID NO: 1, adenine at a position corresponding to position 13319 of SEQ ID NO: 1, or guanine at a position corresponding to position 13516 of SEQ ID NO: 1, and using its semen for fertilizing a female animal.

10. A method according to claim 9, wherein the female animal is in vitro fertilized.

11. The method according to claim 9, wherein the bull is further homozygously cytosine at a position corresponding to position 12195 of SEQ ID NO: 1.

12. The method according to claim 9, wherein the bull is homozygously guanine at position 3117, cytosine at position 12195, a guanine at position 13244, an adenine base at position 13319, and guanine at position 13516 of the STAT5A gene.

13. A method according to claim 9, wherein MOET procedure is used.

14. A method according to claim 12, wherein said female animal is also homozygously guanine at position 3117, cytosine at position 12195, a guanine at position 13244, an adenine base at position 13319, and guanine at position 13516 of the STAT5A gene.

15. A method for selecting a dairy cattle animal as a breeder for desirable fertilization rate or embryo survival rate, or both, the method comprising obtaining a nucleic acid sample from the animal, determining the identity of a nucleotide of the STAT5A gene of the animal corresponding to at least one position selected from the group consisting of positions 3117, 12195, 13244, 13319, and 13516 of SEQ ID NO:1, and using an animal as a breeder only if the animal has guanine at the position of the STAT5A gene corresponding to position 3117, guanine at the position of the STAT5A gene corresponding to position 13244, adenine at the position of the STAT5A gene corresponding to position 13319, or guanine at the position of the STAT5A gene corresponding to position 13516, of SEQ ID NO:1.

16. The method according to claim 15, wherein an animal is used as a breeder only if the animal has guanine at the position of the STAT5A gene corresponding to position 3117, cytosine at the position of the STAT5A gene corresponding to position 12195, guanine at the position of the STAT5A gene corresponding to position 13244, adenine at the position of the STAT5A gene corresponding to position 13319, and guanine at the position of the STAT5A gene corresponding to position 13516, of SEQ ID NO:1.

17. A method for selectively breeding dairy cattle for improved fertilization rate, comprising selecting a female animal whose STAT5A gene is homozygously guanine at a position corresponding to position 3117 of SEQ ID NO: 1, guanine at a position corresponding to position 13244 of SEQ ID NO: 1, adenine at a position corresponding to position 13319 of SEQ ID NO: 1, or guanine at a position corresponding to position 13516 of SEQ ID NO: 1, and fertilizing eggs from the female animal with semen from a suitable bull.

18. A method according to claim 17, wherein the female animal is in vitro fertilized.

19. The method according to claim 17, wherein the female animal is further homozygously cytosine at a position corresponding to position 12195 of SEQ ID NO: 1.

20. The method according to claim 17, wherein the female animal is homozygously guanine at position 3117, cytosine at position 12195, a guanine at position 13244, an adenine base at position 13319, and guanine at position 13516 of the STAT5A gene.

21. A method according to claim 17, wherein MOET procedure is used.

22. A method according to claim 20, wherein said bull is also homozygously guanine at position 3117, cytosine at position 12195, a guanine at position 13244, an adenine base at position 13319, and guanine at position 13516 of the STAT5A gene.

* * * * *

SEQUENCE LISTING

<160> NUMBER OF SEQ ID NOS: 44

<210> SEQ ID NO 1
<211> LENGTH: 18120
<212> TYPE: DNA
<213> ORGANISM: Bos taurus

<400> SEQUENCE: 1

```
caggagcccc ggccgggagc gagcgccggc ccagtcgccg gaccgcccgg cacgaccagg        60
tgggtggccc cggcagcgcg ccccggcga cgcgcgccca gagggggcac cctgctgctg       120
ctgctgctgc tgctgccgcc gcccgggtcc tcgccccgca ggccccggag cccgacagac       180
ggaggggcgc tggggacggt ccccgggacc cagggagagt ttcggcgccg cgtggactag       240
ggacgcggga cgcggatgga gggaggaggc cgagggtggg cgccgtcctc gccctcggtg       300 ggcaggggc gctgtcggac tggatagtgg gagacgtcgg ggcacagcga ggtgcggggg       360
gcgcagcccg agagagggag tgtcttgtct ccccagccct ccctcctaaa caccccagcc       420
acgtgccagc ggtggccgag ccgtccaggg gaaaccttcg gtggccttgc cctagctttg       480
ggctggaata tccccgcgtt cccagaaact gagactcggg gttcgaagca gggtaggggg       540
tgtttgcagt cctccccaga gggcccgagg gcctccgcca tcaagtttct ctttcagttt       600
ctagctgttc ccccaccccc caccccggga agccccggtg gggcgagggg agaggaagaa       660
ggggagggca cctgactttc gggagcccct ccccaagcct cagcgggttc ctcgctggag       720
ggaaggacgg ccttcccctc ctcaccgtct ttcttcccgc acaggaaagc gtgtctgtgg       780
gaggggaggg gcctggcctg accgcggtcc agggatgggt gggcacggca gggccagggg       840
caggcccagt ccacgcctgt gacgagaagg cacctcctca gcgctctgct cgccctaggt       900
gaacggacat ggcgggctgg atccaggccc agcagctgca gggagatgcc ctgcgccaga       960
tgcaggtgct atacgggcag cacttcccca tcgaggtccg gcattacttg gcacagtgga      1020
ttgagagcca gccgtggtag gtgccctgc ccggcgcctt gccctgctgg tcgctaacca      1080
tcaaggcccc ttggccttta cgtctcctct tggtggtttg gggagattct gatcctggct      1140
gtccctcact gtgtggaagg ggtggtgtcc cagggaaagg ggaacaggga aatgggagtc      1200
tgggagggga gaggggatgt ttctagactc tgatggctgt ggagctgcag ggagcaagtc      1260
ttgtgggcag gagcctggga ttttcccgtc cttcctggta cctgacctcc tcatccgagg      1320
aggcaccata gcaggtttct ctctcctgcc ttgcgctaag ggatgccatc gacctggaca      1380
atccccagga ccgggcccag gccacccagc tcctggaggg cctggtgcag gagttgcaga      1440
agaaggcaga gcaccaagtc ggggaagacg ggttccttct gaagatcaag ctggggcact      1500
atgccacgca gctccaggtg ggcgtgagct gcaagccgtc tgcagggaaa cggtgtcggc      1560
cttctctttc cagcaccaga acccctgggt tttttcctgg tttggccact gactcactgt      1620
atgaccctga gcttatctgt gcttcaattt ccccaccccc ctctttctaa atcagacctg      1680
tcagattccc ttagcctatg acaaagtaag agacggggca tgtttgtccc caagagaagg      1740
gggatgggtg aaagcacttt ctgggtagat caggcagaag ggatgggagt agcctgagtc      1800
aaaattctgt tgttgagaga aacgaacacc gacagattct agaaaggagg ggatgggcaa      1860
ccagacagct ctcttggggc aagtggcgag cgagaggagc agcgttgtcc tggagccttg      1920
aattaagggt ttaatgtaag gtgagggtgt gggaggaagg agtaaggggg aaagaggaaa      1980
tttttgtgga aataggaaag ggatgtggat ggtaatcata gatgagcatt tattggaact      2040
```

```
cacttgaagt tttagagagc cttcttgaat acaagcagca gggtgccaag gaaataaaaa      2100
gtccatccca aaggaggcag gaaacagaag aaacctgggc tgtgggggt  gtgggaaggg      2160 aagtaaaata ggaacccagg gccaggacta taatggaaag taccttgacc ttggcattag      2220 atgcccgag  tcttgagtca tctgctcact cacttgtttg cctttggaca agtactcaat      2280
ctctctgagc atcagtattc tcatctgtga aatgaggata atggtttctg cttgtgttat      2340
agggtttcta tgatgcacaa gtcaaaggag atggcagatt ggaagtactt tgtaacctgt      2400
ggctttctaa tgcagtgtga accgaatgtg aagatctggg aggggaaatc aagtcaagga      2460
gagatagagg ttctggtggc agttcctgag gcttccgagt ggaagctgag gcataggctg      2520
gaggagagga aggagtgggt ggcactgcag tgggcatggt gggagcagag ggtggccttt      2580
ggtagccact gttggattct ttcagaacac gtacgaccgc tgccccatgg agctggtgcg      2640
ctgcattcgc cacattctgt acaatgaaca gaggctggtc cgagaagcca caatgtgag       2700 tgtcccatgg gtttggggaa agattttgag aagtcctttc acctgctctc ctctccagac      2760
acagctctgt tttataaata ctggcaagag agagcaccaa agaaataaaa cacacaggca      2820
agtgtgagag gccatattac atgcaggttt agattgaccc cacacacaca cagagccccc      2880
actccctggc tctatttact agctgtgcga cttgagcaag ttacttcacc tctctgagcc      2940 tccgatttt  tcctattata atgagggca  gtcacagtat ctactctata ggctatttc       3000 gaggattaaa tgagatacca tgtgggcaaa ggatgtgtgc tgtgtgttta atcgttcagt      3060
cgtgtctgac tctctgcagc cctggggact gtagcctgcc aagctcctct gtctgtagaa      3120
ttttccaggc aagaatactg gagcaggttg ccatttcta  ctccagggga tcttcccgac      3180
ccagagatca aacccacatc tcttgtgtcc cctgccttgg caggtggatt ctttaccact      3240
gagccacctg ggaagcccag agcaaagaac agacatatac aaatgaagaa gaggaagccc      3300
taaaaacata tgcacatctg gaaactcaat ctatgtcaga gatggcatta caaatcacta      3360
gggaaaagat ttgtcattga ataaatgagg ccggggcaaa agaagaaata tcctctggcg      3420
gggtctatga ggagaaatgg aggtctgtgt cagaagaatt aacctgggca agctcagaga      3480
agcaaggccc agggaggcag agcagggacc tattccccag gttctgaaat cataaagatc      3540
tcggacatat gcttcgacag tggtgcaaat ggtacattat ccacagtaaa gcaaatgaa       3600 tttcattaaa tgatatccct taggtaatga ccacagaata atgcctgaag tgaagtcata      3660
gttattattt acttgtggtg gacactgata tcaagaattt gagaggtcat tcagtaaaca      3720
tttatcgagg tcctgctgtg cgtctgacac tggactagga tgggagaaac agataaagtc      3780
ctggcttcca cctaaaaggg atttgggctg tgatagattc tttaggactc tgctgagtgc      3840
taagtcagcc tatatggaaa aaggacccaa ctcagattgg ggcaggctgg ccagtagtgg      3900
ggagggtgtc cagaggaaaa agatgcctga ctgtaatgag gaaagaggga ggaagaaggt      3960
ggaatgagtt ttctagtgaa aaatagcagc agtaggattt ccctggtggt ccagtggtta      4020
aggccccacc ttccactgca ggaggcatgg gtttgatccc tggttgggga attaagatac      4080
cacataccac aaggtgcagc caaaatagaa ataagaaa   atgcaaaata ataaatagc       4140 aacagtatat atgagggcag gaaggcacaa gccatcttat gacatttgaa gaattttaag      4200
tgtttagtga tcctgggaag aagggagccg actgggcaga agccaggtca cagagggtta      4260
actggtacaa ttcttgactt ggtgcaatta cagagctatc tgtaaacgta ggaatgagtc      4320
cagttccagt taagaaatac ctgcctacaa ggcaggtgct gttatgtttg ggggaaaaat      4380
agtcctccag tcatcaagct gttcttggac acctctgacg ttctgggcct tgaggatttt      4440
```

```
gttgtgcacc aaatgggaca aagtcttggt ccttagggag ctcactttct agtgcagaga    4500
ggcagacaag aaagaacatg caggaacatg acacgttcag tagggcagtc ctattttaat    4560
gtaactcttc agaagaggtc actctgaaaa ggtgccagtg gaagtgccag cctcaggagg    4620
atttagtgcc agaatgttcc agggtaatgg aacaaaacat gcaaaggccc tgaggcagga    4680
actccctgcg tatccaagga acagaaagtg gccagtgtgg tttagcaaca agggagctgg    4740
gggtggggta ggcagaggct cctggctagg gccgtggagg ctgtgaaggg agtttggggtt   4800 ttattctgag agcagtttac tggagaggcc ctaaaaattt ggttgaggac tgccctggga    4860
gcccagtgct taagaatctg cctgcccatg gcggggacat gggttcaatt cctggtgccg    4920
gaagattcca aatgccatgg tgcacctaag cccatgggac acaactactg agctctagag    4980
cctgtgctct gcaacaagag aagccactgc aatgagcacc acagctagag agtagccagc    5040
ccatgagcag taacaaagac ccagcacagc ccaaaataag taagtaaaat aaaaacaaga    5100
acagcacttg gttgaaggaa tagatccaac cggattagct gaatggctgg atccacaaag    5160
cctttgttga tgcctccttg taccttcatt tgggggtctt caggactcca cccacgagca    5220
gttcacactc ttccctcagt cctgaggtct tagtgaggac acagaacgta tgttcacatg    5280
gctttgttcc ccatcatgtc cccagcatct agcatcatgg catgggtca gtgaatgact    5340 gaaatgaggg gccatcatcc ttagtaggaa aactcaggta actcctggga tgggttgggt    5400
tctagtctct ccagagagaa ctcaaatgga ccttgtgtgg ggtactcaga tggaggtcag    5460
aactgcaaca gaagttttcta ccagagtctg ccaggtcacc tatttctcgt cctttacccc    5520 ctacaccccct attttggcaa atgactcttc ttctgactca aagtacccctt ccttcttatt    5580 ctagatttgg tgtctgggt ctgtagtatt ggtgttcccc aaggcctgag gttttctcc     5640 catcctcact gcccagctca ctgctgcctg caccctcccc tgatatgtct ccagggtagt    5700
tcttctgctg ggatcctggt tgatgccatg tcccagaaac accttcagat caaccagaca    5760
tttgaggaac tgcgactggt cacgcaggac acagagaatg agctgaagaa gctgcagcag    5820
actcaagagt atttcatcat ccagtatcag gagagcctga ggatccaggg tgagcctggt    5880
gtgggagggc agtgcatgtc tggaggacca gagtgagacc actttgtgaa ctcctgcagg    5940
gttggggctg ggtccatgtc tgtctcccca gagccttacc caaagcttgg gacaagtaac    6000
ggctccagtg atggagcccc tgctgtgggc caggctccag gctaaaccct tattcaatac    6060
aacctttact caatacgact gtgttattca acacaacttt taccatagcc ctaagaatta    6120
agtgggtttt ccctggtggc tcagatagta agaatctgc ctgcaatgca ggagacccag    6180
gttcggttcc tgggtcagga agattccctg gagaagggaa tggctcccca cttcagtatt    6240
ctttattcct gttttgcaaa taataaaact gatgttcaaa gagaacatgc aattggcct     6300 gggcttcttg taagttgcag aactggatgt taactagaga tattcataaa atccttatat    6360
tttattaacc agtattttgt atctcggtga aagaatgaat gaatgtggac agtgttcccc    6420
aatcagaggg aaaacctagg ttgggagtcc cctggttgaa ccaggctggg gagaggtgga    6480 acccaggaa tgccccttct tgagcttcac taataggagg taaagatggg aggaggacgc    6540
gacagtggaa aactctgctg tctcccaggt ctataatttt ctagtagctg ccatgattag    6600
ggtgtggggg aaaattaac ccagaaggaa ttaaccccac taagtgtcct tacggtacac    6660
tttgaagagc cttgaaacat gactcatctt cctccacttc aaattgaccc cagagctgta    6720 tcaccccat ctaagtgaga acaggaagcc acctttttcct tgttcttatt tttctgactt    6780
cttaaggtag aacctcaggt cattgatttt agacccttct ttttctaat gtatatattc     6840
```

```
agagctactg atttccctct cattaatgct tcagctgcat ctcatcatct tggatatgct    6900
gtataccatt atcattcaat ttgaaatatt ttctaatttc tcttctgttt attttaccca    6960
tacactattt agacgtatat tgtttaattt ccaaatattt gagttttttc tagatgtcat    7020
accattattg atttcatttt gtggctgagg tctattgttg tcagagaaca tatgcatatg    7080
atctcctctc ttaaatttat gaagacttgt tctgggcccc ggcatgtgct ctatcttgat    7140
gaatgtattt tgtggtcttg aaaagaatgt atgttctgaa gttgtttcat ttaaaagtag    7200
caataataaa ttcaataatg ttaatgtatt taacattgta tataatgcta acataatgaa    7260
gtaaaaaaac aaacaaactg agaaaccaat aacatctata ttttccaaac ataatttagt    7320
gagtagagtg gcattgtttt ttacattttt acaaatattt tcaatgttag cttagtcgg    7380 agatagctgg atctggcttt caatctgttg taatatcaca tatcttatag cctctagaaa    7440
actctgctgt atacttataa gtgaataaaa gaaaaaagg caaataaagt cttatgatta    7500
aaaaaataat aataaagtca tgattttatg aaaatagttc tggctttgtg gacctcctat    7560
aagggtttta ggaaaccttc aggggtccct ggctcacact ttaggaacca ctgatacatg    7620 tcttattga tttatttttg cctaattgct cctatagata gagaggtagc aagatctact    7680
gtattgtgta attctccgat tacttatgta aatatttcct ttatgttttt tgaagcttta    7740
ttatttgatg catatatatt tatgccatgc ttattcgctc agtcgattcc ctgggtcagg    7800
gagatcccct ggagaaggaa atggcacccc actccagtat tcttgcctgg agaatcccat    7860
ggatggagca gcctggtagg ctacagtcca tggggtcgaa cagagtcgga cacgactgag    7920
cgagctcact cactttcact tttagtctcc cagtcatatc caattctttg tgacctcatg    7980
atctgtagtc tgccaggctc ctctgtctgt ggggattctc caggcaagaa tactggagta    8040
ggttgctagg ccctcctcct ggggatcttc ccagatgctg gaccagatca gatcgaaccc    8100
aggtctccca cattgcaggc agattcttta ctgtctgagc caccagggaa gcatatatgt    8160
ttatagttat ttataattag tatgtctttc tgattgattg accccttaat aattatggaa    8220 tagcttttctt gatctctggt atccctcttt gtctggggtc aaatataatg ccttcagcct    8280
tttattctat attaacacaa tgtattttt catgcttttt atttattttt tattttaaa    8340 ttaatttatt tattttaatt ggaggctaat tactttacag tattgtagtg gttttgcca    8400 tacattgaca tgaatcagcc atgggtatac atgtgttccc catcctgaac cccctccca    8460 cctccttccc catcccatcc ctcagggtca tcccagtgca ccagctctga gcatcctgtc    8520
tcatgcatca aacctgggct ggcgatctgt ttcacatatg ataatatagg tgtttcaatg    8580
ctattctctc aaatcatccc accctcgcct tctcccacag agtccaaaag actgttctat    8640
acatctgtgt ctcttttgct gtctcgcata tagggtcatc attaccatct ttctaaattc    8700
attagtatac tgtattggtg ttttcattc tgacttactt cactctgtat aacaggctcc    8760 agttcattc accttattag aactgattca aatgcattct ttttaacagc tgagtatata    8820
tgtaccacat ctttcttatc cattcatctg ctaatggaca tctaggttgt tccatgtcc    8880 tggctattat aaacagtgct gcgatgaaca atggggtaca cgtgtctctt tcaattctga    8940
tttcctaggt gtgtatgccc agcagtggga ttgctgggtc atatggcagt tctagttgca    9000
gttttttatt catgctttt aaaatttgaa atgtagacag cacataattg agtcttttg    9060 tatttattct gaaaatcttt gcttttaatt gaggtgttca gtttattaat atttaatgta    9120
atgttaaata cccgtctact gaggtccaca ttttaatatt tatttttgttt tgtcccttt    9180 tggttttttg ttcctctgtt cttcctttta attctttaaa tttttaaaga tgctgcttta    9240
```

-continued

```
acttaaccat ttaagctttc ctcctaccct accctatggg tgttttctgt atcttgagat    9300
taacgcattg cctgagactt agcaggcatt gaataaaagt tgggggatg attcaagcag     9360 gtcttcatta catctgaatc catcccagat taacgtgaaa gaaaagacag cccttttcca    9420
agattaggga ataggagatt caggctctta tttctaccca aggccattga ctggctgaca    9480
gaatggatga tccgcttctt gggttttctg tttgctactt gtgaggttgg gtttgtcccc    9540
atcatgcaat gtcagttcag tctcatttat caggtgcacc catcagaaac acagatgact   9600
gatctgtttg tgtgagggca gtctcagctc cctccagtgg agcagacaat tgcctcacgt    9660
ctcctggcgt ccttcccaga agcttctgca atttgccagg agagacttaa gtgggttact    9720
tgcataagga agccaggtcc cggtgttggg attatcactg tctccctgtg ggtggcagga    9780
ttccgagtgg ctgtccagat tgttctgctc cattccttgc ctgctcagtc ccctgcagtc    9840
agaatggagc catatttcta agttctcttg aatagagttg ctttagtctg tcccagccct    9900
gtgtgtccat aggaccgggt cttggccatg tgacatggcc ctcagaggcc tgcaaggagc    9960
ttgaccaaga cttgctgact gacgctcacg tcttctagac tcagcccag tgaggtccct    10020 gggatgttca gaaaggccat tggcgagggt aggatgccag cactgggac agtggttacc     10080 tgtggaggga gggatggggt tgccagcagg ggaggggtac gggtgcttca ccatggaagt    10140
gcctgatttc ttaagcggct tcttgataca caggtgtttc ttgtatcatc ctctctactt    10200
cctgtgtctt aagtatttca tcacaggttg tttgcagagg gagtcagtga ggcctggtta    10260
catattcctg ccattgatga gcggcctgag agctggtgtg gagagaaatt gcctctctct    10320
cctgagagaa tctcactgct tttgtgtccc cagtggcccc gactctctct gtgtctcatt    10380
tccggttggt tagctgagct cacagtgacc aacctggtta agcatgttag ggaccttcac    10440
cacctgaaga aaaccccctt ccctgaggag aggctgccaa gcctggtagt caggacaaag    10500
cccacggacc agaggcttct cacgaggctg tgcccgtgag gttggggctg agagctgctc    10560
catctgcctt tcatcccctc atgtaaccca ttaaccataa ctgacttccc tcgggggcca    10620
atggtgccag gcagcttcct gagcattttc tgtctcatca cttagcagca gccgctgaag    10680
tagatgcctc atgatgctcc cctttttacag atgggaaaac tgaggcatag gagagtgggg   10740
tgacttgccc aagttcacca cctggtgaat ggcggggttc acttcagacc agacatggtg    10800
gctccaagcc agaccatgca ttgggtgagg caggctaagt aggggttgg ccagggcagg     10860 cttctcctca gctgtccccc aggcttccat ctccccactc cctgagagga gctcagagtc    10920
gggccacagg ggccagagtc ttctcatcta cgggccccgt tgctgtggaa cctgactggc    10980
cgctggtcag acatgtcccc tcgagggtct tgcctccaga acagatgggc tcccggctgg    11040
accggggagg tcatggtcgt ggtgtcctgt cccctcctcc agctcagttt gcccagctgg    11100
cccagctgaa ccccaggag cgactgagcc gggagacggc cctccagcag aagcaggtgt     11160
ccctggagcc ctggctgcag cgcgaggcc agacgctgca gcagtaccgc gtggtgagtg     11220
ggctcagcgt ccctccctc ccgcagggc agtgacaccc tgagctgtcc tggggaccct      11280
gagggaggca gagagccagg aggagagcgg gacccagcag agcaggaggc ccgggccttc    11340
ttcctcatgg ggcctgaggg ggagagtcgg tctgggagga ggaggccctg cagggctgtt    11400
ctgagagccc agaagggccg gctgagccac cgcccgaccc tcaggagctg ccgagaagc     11460 accagaagac cctgcagctg ctgcggaagc agcagaccat catcctggat gacgagctga    11520
tccagtggaa gcgcggcag cagctggcgg ggaacggagg gccccccgag ggcagcctgg     11580
atgtgctaca gtcctggtac caggggtggg gggcggggag gggcaggcag cagagtggtg    11640
```

```
ctgccagctg ctgtttgcgc ccacgtctac atgagcagct ggctccctct gtctgggcgc    11700
gggtcttatc ccaccagtgg tgtgtttggt gctgacaccg tgtcccttt ctgtgccccc     11760 tccctggga ggatgctggg gtggggccag gtggcaaagt ggcgctcagg ctggttggac     11820
cccagtcagt gtcgctcctc ctgggtgttt ctctggtttt tttggaaggc agggcatctc    11880
tgctgtgccc agtgcacagg cgaggtggct cgggcaccag gccttcctgg gggtggagct    11940
gggtgtgggc cttgtcccccg cctgggcgcc tgccagcttc tggcctggag gacggggggtg  12000 aagcccgtgt ccttcccttg ggccctgggg ctcgggttca ggtgtgagaa gttggcggag    12060
attatctggg agaaccggca gcagatccgc agagccgagc acctctgcca gcagctgccc    12120
atccccggcc ccgtggagga gatgctggct gaggtcaacg ccaccatcac tgacatcatc    12180
tcagccctgg tgaccaggtg actcctggcc acgccccgct cccatctggt tgccctgggt    12240
tgggggcagc agggtctttg cagatgggga gctctggctt aaatccttca gtttctgcct    12300
cacaccctcc tcccatccct ctccatcccc tgttgctatg gcctcttgct gtcgacctca    12360
cccagtattt ctcgtggaca ctacacgggc atttgtctcc tgcaactcct ttcagctgct    12420
gagttccttt tactgcctcc cttcccgcca gctcccctga ctcacagtgg ccccagggag    12480
ggtggactgt ccgcaaaccc tcccttcacc tgctcagcct ggtgcaaggc agcctcccca    12540 cgtgaaggt ggggccagag tcctgtcccc tgaagtgtct cctgtccctt gtgtctccgc     12600
agcaccttca tcatcgagaa gcagcccct caggtcctga agacccagac caagttcgcg     12660
gccaccgtgc gcctgctggt gggtgggaag ctgaacgtgc acatgaaccc cccccaggtg    12720
aaggccacca tcatcagcga gcagcaggcc aagtcactgc tcaagaacga gaacacccgc    12780
aagtatgctg cccgctccctt catctgccct cccccagctc agcctctgct ctgtagctgg    12840
ggtcccaggt gatgaggaca cacggggcct cccactcttt gtctagcatt gcaatgacag    12900
atgactctgt ctgtctgggg gtattcctcg cacacagagc aaatcaagga cttcactatt    12960
agggtgtccc aggatctgtg ctgagcactg gcacagtgct gggatccaca ccaaacttgg    13020
ctccatcacg gcccaacctt taggctagca ggcagcagac gtgagaattg attacttgct    13080
ggcatgtgaa aagagagacg actggggcac catgaaagtg ggtcatggag ggggtgggac    13140
agaatgacag ctagtttcaa ggctgcgggg tgactaggag gagatggtga acgggcgtgg    13200
agagggcaga cgttcgggca gagagaacac gggcctgtct ggaagaggag cagacaaagg    13260
gcgtggtgga tggagaaccc ggggtgaggt cctgggatta ggccaggcca cccgtgaagg    13320
gcgtgggagt gagtgaagga gggcgggaat gagtgagggg agagactggg tcctgagtac    13380
tgaggcccac tgtgtgctct ggggctagga tgacgaagat gacgaagagt tctcactctc    13440
ttagagcctg cctttgggct gggaacaaga cagtcatata ctcttaaaaa tcaggcagcg    13500
tcagaaggca atagattcta gacagaaaat taaagccaag caatatcaca gcgcctggat    13560
agatgttgca acagcacatg gatggccaag gagggccttt ctgaggatct atttgagtgg    13620
agacctgaat gagaaagtca agaatgcaac aggagaattt gcctggtggt ccactggtta    13680
agactccacc ttccaataca gggggtatgg gttagatccc cggttgggaa actaaggtcc    13740
catatgcctc ggggtacagc cagaactttt taaaaaattt aaaaaatagt aaagtgcaaa    13800
atgcattact taaaaaaaga atgtaacagg aaggcaagta caggagtccc caggcagcac    13860
tgagcttgtg tgttcagcaa acagacaaga tactgtgggc ttgcttgttc tgaatgaggg    13920 gagggggagcc cagtgaggcc agggcagggg ttgatggcat ggatcttgtt aggctgaggt    13980
catgattttt atgtcaagtg ggctagaagc tgccaaaggc ccccacgtca atcttgacgc    14040
```

```
ccaaggaact ttaacattgg ccccacccct ggggctttgc tcggatgctc tcaggttgat   14100
gaggaaagac agcccagagg aacgctctta ggggaggggt caggggctgc tgtggggcct   14160
tctggagaag ctgggccca gggtgcatac aggacagtgc tctgggcctg ggcccagcgg   14220
agacgggttc ccctctgctt ggcagtgagt gcagcgggga gatcctgaac aactgctgtg   14280
tgatggagta tcaccaggcc acaggcaccc tcagcgccca cttcagaaac atggtgagga   14340
cagggcccgg cccgagctgg gaggtctgtc cagagctgag tcctgagtcc tcgtaacctg   14400
ccacgttccc ctcgtcccct tttgatctcc caccctgcag tccctcaaga ggatcaagcg   14460
agctgaccgg cgaggtgcag agtctgtgac ggaagagaag ttcacggtcc tgtttgagtc   14520
tcaattcagt gttggcagca atgagcttgt gttccaggtg aaggtgaggc ctggctcccc   14580
tgtcccctgc aggccaccca gctgacttgg gaaagccaga gactggaatc cttgcatacg   14640
ctcagtccag ttaccgcatg atgctctcag aaaacctaat ttcactctgc tggtgcttat   14700
ttgctagatt gtaatctggc acctgggctt ccctggtggc tcagatggca agaatccac   14760 ctgcaatgtg ggagacctgg gtttgatccc taggttggga agatcccctg tgagttaacc   14820
cactccagta ttcttacctg gagaatcacc atggacagag gagcctggcg ggctagagtt   14880
catggggtcc caaagagtag gacacgacag agtaggacac gactgagtga ctgagcacag   14940
acagcaatct ggcacccacc ctcaggattg aggcaatggc caaaaagaaa tgggctgtgt   15000
tttttgttta tttctgcttt ggttttgctg aagggggctt gaggaatggc ggtcaggtgc   15060
ctcccccaag tggagggcaa gaccagggtc ataggccctc atccctcatt ccctggattc   15120
ccgtagaccc tgtcccttcc cgtggttgtc atcgttcatg gcagccagga ccacaatgct   15180
actgccacgg tgctgtggga caatgccttt gctgagccgg tgagtccccg tgggacccc   15240 acctcagccc cagcccctca gaggttccca gggccagccc caaccccag ggctcctgct   15300 gagtggtctt ctcccaccct tgggccaaac cagtggtcag ggggcagctg tgtgagcgc   15360 cctgccctca gcacgacctc agctctgtct gggctccagg tcacgggact ggggtctcct   15420
aggtctgtga gcttggtgct tggaatctgg cccctgatct ctgctcccag gctccgttc   15480 tgggtctcta cccctatata cccgtccctc tgctcctgcc ccccgtttct ttccattgtg   15540
cttttgtctc cttttcctgga tctttctcac tcccctctgc ctcttggtat ctgtgtgtgt   15600
gtgtgtgtgt gtgtgtaaat atctcctatt acctcaatct tttccctttt cttctctccc   15660
tctcagggca gggtgccgtt tgcggtgccc gacaaagtct tgtggccgca gctgtgcgag   15720
gcgctcaaca tgaaattcaa ggccgaggtg cagagcaacc ggggcctgac caaggagaac   15780
ctggtgttcc tggcgcagaa gctgttcaac agcagcagca gccatctcga ggactacaac   15840
ggcatgtccg tgtcctggtc ccagttcaac cgggtaaggg acgcattgcc tgctgcctgc   15900
ctgggactat ctctaccct ccccacctca cagacaggca cctggtccat gggcccctc   15960 cacccccaga cccctctcct acaaccagga gagatggggg ctggtgcccc aaggagtgga   16020
gacagccatg agacccgagg caagactttg gaaagaaccc agagctggaa gtcagggtcc   16080
ccgggctctg gtcctcaaca tgttacctca tttgccaggc cccttccgtt ctctgcatcg   16140
cacttttccc atctgtagaa tgaagggggtt gggcaggaat gactttggag gtctcatcca   16200
gcttggacag tttcttgcac cttttgacccc ctccatggga ttgtcccaga tccctgtgtc   16260
tgagaggatg ggcttcccag gtagcgctag tggtaaagaa cctgcctgcc aatgcaggag   16320
ataaaagaga cgtgggttcg atccctgggt taggaagatc ccctggagga gggcatggca   16380
acccactcca ctattcttgc ctggaaaatc ccatggaccg gaggctggtg ggctatagtc   16440
```

-continued

```
cataaggtca caaagagccg gacacgattg aagcgacttg gcacacaggc actgggtgag  16500
gacacagggg caccaagtgt tccctggacc acctgagatg atggggacac aagccctaac  16560
ctgggctttc ccgggcaccc tcaggagaac ttgcccggct ggaactacac cttctggcag  16620
tggttcgacg gggtcatgga ggtgctgaag aaacatcaca agcccattg gaatgacggg  16680 tgaggcatgg cgggtgggag gtcggggctc aggggacagt ggctggtggc ccagcagtga  16740
ctctgtgtgc tccatgcacc cagggccatc ctaggttttg tgaacaagca acaggcccat  16800
gacctgctca tcaacaagcc cgacggtacc ttcttgttgc gcttcagcga ctcagaaatt  16860
gggggcatca ccatcgcctg gaagtttgac tctcgtgagt tccctgcatt gcccacactc  16920
ccgccccagt ggctctgttt ctcatttcct cattcccatt ctccatcagg cctgtatcct  16980
tagaaggggt ccagtgggaa agatgggaac tgagcttgga gggtgggtgg agtgttgttc  17040
aaatacccag tctctattgg tttcctcttg ggagaaccta acatcactac cccccacagc  17100
ctccagaact gctgagcgag tccttctttg tcctgaccca gacttgttgg tatctgctcg  17160
cccgtggtca cttccttgcc ctgtgctgag aacaggggtg gggtagcagt gcaggctttt  17220
acctggatgt ctccacaagc ctggccccca gccctacagc tccaatcctc ctcctgtggg  17280
cagtgggttg tgaaaatgag cttggccttt tcacagctga ccgtaacctg tggaatctga  17340
agccattcac cacgcgggat ttctccatcc gatccctggc cgacaggttg ggggacctga  17400
actatctcat ctacgtgttt cccgaccggc ccaaggatga ggtcttctcc aagtactaca  17460
ctcctgtgct tggtgcgtct gcccaacact cctcccaaca cactcccggg gctaagcagc  17520
gggtacaccc caggaagagc ccaggggccc tttcccctgt gagggctggt ccgtgggatg  17580
gcacaaggca cgcagagggg atttcagggc tccgtgcacc cagggccatc ctaggttttg  17640
tgaacaagca acaggcccat gaagcggaaa ccccgaccta gctttcttcc ctgcaaagca  17700
aacactgagt gcactccctt ctgcgcccttt ggaggaggag gcggctgcag tgtaggggga  17760
ggagcaggat cacgcagacc cacagataat gcacggctcc catcttaatc aactgctctc  17820
acccctctcc accctcaaac ctgccctcac agttgagggt aggaagcaaa atggacaggt  17880
ttttttctct tcaacctggc cccactcctt tggttgggtt tgttcctcgg tgtggactct  17940
gtttccttgg caggggtggg gacggggaga gaggaagcca agggccagga aaggaagcgg  18000
gacatgggat gagactgaaa ccagaggtct gggggtcac ctggtgactg tcagcaggtg  18060
ttcaatgggt ctgtgggaaa tcttatccct gatgagcccc gtggcattgt ggggagtggg  18120
```

<210> SEQ ID NO 2
<211> LENGTH: 1716
<212> TYPE: DNA
<213> ORGANISM: Bos taurus

<400> SEQUENCE: 2

```
gccacagatc aagcaagtgg tcccgcagta agtgtccggg cccagcgctg gtctccagct    60
gcctcttttc tcctccccgc gcggctccac ctggctctcc tcaccccccca ccgcctcccc   120 tcctattccc tcccccaccc aacttggccc agccctgggg aggggaactg ggcgtggtca   180 caagggggcgg gtacccaggg ccccgcccct gcaccggagc cctaggctca ggggccagtt   240
gtccttccac acctgagaaa gacacgaagg tgccccgag cccctccccg ctgaggctcc    300
gcttcctccc acaggtttgt gagcgcctct gcagactctg ctggaagcaa cgccacctac   360
atggaccagg ctccttcccc agccgtgtgc cccagcctc actataacat gtacccacag    420
aagtaggttg tgttctcatg cagctccatg tacccacaga agtaggttgt gttctcatgc   480
```

```
agctccgggg ggaggaaccc agagggctaa tgggcaagga caccagagct cctctccgtc      540
tgagaccacc caggccaggt gggcttgggt atatgcccag gtgcagggtg gatgagatca      600
gccaaccagg agcacagagc attgtgaaat agcaggaccc ttgctctggt gctgagtagc      660
tgtgtgacct tggggaaatt atggagcctc tctgatgctc agtttcctta tctgtaaaat      720
ggaggcaaga gtacctacca catgggactg gggtcaggct caagcaagag actgcaggta      780
atgcatttag cccaggtaag gctgttgtaa tggcttgata cagagtatct ctgggtggtg      840
gtggttctta ggagttgtgt gggaacagga catgtctctc ctctctgaag ttcccagaga      900
agaaaattca ttctctttcc agccaagggt ggcctactgc catgggatga ccacaggctt      960
gggagtcaca aaactggaat tccagtcctg actccacctg cctaccaggt ggctctgaac     1020
aagcttccta acatggttga gcctcagttt cttcctcagt ggctgtgggg attggcataa     1080
agtggttgaa aggcccaggc cttcataggt gctcagtgtc tcgtgcctga tctcatgg      1140 gcagagctcc ttcacccaac cacctgtttt tacagaggag ggcagggaca ggggaaatga     1200
attccctgag atccctcagt gagcttgtga gtgatgagac tagaaccggg gtgtcttccg     1260
acaaactagt gactgactga ttcagcttgg tggtgcgggc atctagccag agcaggtcct     1320
gttcccatga gactgaacgg ggatcaggct gggcgctgtc ccccaggagc ctggggctct     1380
gcggcaggcc agctccctct gatacccctc tccccctccc agccctgacc cggtgctcga     1440
ccaggatgga gaattcgacc tggacgagac catggatgtg gcccggcacg tggaagaact     1500
cctccgccgc caatggaca gtctggagcc ctctctcccc ccgccactg gtctctttac       1560 ccccggcaga ggctcgctgt cctgaatgtt tgttcgaaca ctgcactcct ctgtggaaac     1620
aatccccagt gtgcagggtc ctattcattg tgattttgta tttgtatctc tgtgcatact     1680
gatgcctttg caggcagccc atgtacacat gtagat                              1716
```

```
<210> SEQ ID NO 3
<211> LENGTH: 22
<212> TYPE: DNA
<213> ORGANISM: Artificial Sequence
<220> FEATURE:
<223> OTHER INFORMATION: PCR Primer AF1

<400> SEQUENCE: 3
gagagaggga gtgtcttgtc tc                                                22

<210> SEQ ID NO 4
<211> LENGTH: 20
<212> TYPE: DNA
<213> ORGANISM: artificial
<220> FEATURE:
<223> OTHER INFORMATION: PCR primer AR1

<400> SEQUENCE: 4
gactcccatt tccctgttcc                                                   20

<210> SEQ ID NO 5
<211> LENGTH: 20
<212> TYPE: DNA
<213> ORGANISM: artificial
<220> FEATURE:
<223> OTHER INFORMATION: PCR primer AF2

<400> SEQUENCE: 5
ggaacaggga aatgggagtc                                                   20

<210> SEQ ID NO 6
```

-continued

```
<211> LENGTH: 20
<212> TYPE: DNA
<213> ORGANISM: artificial
<220> FEATURE:
<223> OTHER INFORMATION: PCR Primer AR2

<400> SEQUENCE: 6
ccttcctccc acaccctcac                                                   20

<210> SEQ ID NO 7
<211> LENGTH: 20
<212> TYPE: DNA
<213> ORGANISM: artificial
<220> FEATURE:
<223> OTHER INFORMATION: PCR primer AF3

<400> SEQUENCE: 7
gtgagggtgt gggaggaagg                                                   20

<210> SEQ ID NO 8
<211> LENGTH: 20
<212> TYPE: DNA
<213> ORGANISM: artificial
<220> FEATURE:
<223> OTHER INFORMATION: PCR primer AR3

<400> SEQUENCE: 8
cacacacact tgcctgtgtg                                                   20

<210> SEQ ID NO 9
<211> LENGTH: 20
<212> TYPE: DNA
<213> ORGANISM: artificial
<220> FEATURE:
<223> OTHER INFORMATION: PCR primer AF4

<400> SEQUENCE: 9
cacacaggca agtgtgagag                                                   20

<210> SEQ ID NO 10
<211> LENGTH: 21
<212> TYPE: DNA
<213> ORGANISM: artificial
<220> FEATURE:
<223> OTHER INFORMATION: PCR primer AR4

<400> SEQUENCE: 10
gatatcagtg tccaccacaa g                                                 21

<210> SEQ ID NO 11
<211> LENGTH: 21
<212> TYPE: DNA
<213> ORGANISM: artificial
<220> FEATURE:
<223> OTHER INFORMATION: PCR primer AF5

<400> SEQUENCE: 11
cttgtggtgg acactgatat c                                                 21

<210> SEQ ID NO 12
<211> LENGTH: 20
<212> TYPE: DNA
<213> ORGANISM: artificial
<220> FEATURE:
<223> OTHER INFORMATION: PCR primer AR5

<400> SEQUENCE: 12
```

```
accctctgtg acctggcaac                                              20

<210> SEQ ID NO 13
<211> LENGTH: 20
<212> TYPE: DNA
<213> ORGANISM: artificial
<220> FEATURE:
<223> OTHER INFORMATION: PCR primer AF6

<400> SEQUENCE: 13
gaagccaggt cacagagggt                                              20

<210> SEQ ID NO 14
<211> LENGTH: 20
<212> TYPE: DNA
<213> ORGANISM: artificial
<220> FEATURE:
<223> OTHER INFORMATION: PCR primer AF7

<400> SEQUENCE: 14
gaagccaggt cacagagggt                                              20

<210> SEQ ID NO 15
<211> LENGTH: 20
<212> TYPE: DNA
<213> ORGANISM: artificial
<220> FEATURE:
<223> OTHER INFORMATION: PCR primer AF7

<400> SEQUENCE: 15
gcccagtgct taagaatctg                                              20

<210> SEQ ID NO 16
<211> LENGTH: 22
<212> TYPE: DNA
<213> ORGANISM: artificial
<220> FEATURE:
<223> OTHER INFORMATION: PCR primer AR7

<400> SEQUENCE: 16
ggcagactct ggtagaaact tc                                           22

<210> SEQ ID NO 17
<211> LENGTH: 22
<212> TYPE: DNA
<213> ORGANISM: artificial
<220> FEATURE:
<223> OTHER INFORMATION: PCR primer AF8

<400> SEQUENCE: 17
gaagtttcta ccagagtctg cc                                           22

<210> SEQ ID NO 18
<211> LENGTH: 21
<212> TYPE: DNA
<213> ORGANISM: artificial
<220> FEATURE:
<223> OTHER INFORMATION: PCR primer AR8

<400> SEQUENCE: 18
cccaggccaa attgcatgtt c                                            21

<210> SEQ ID NO 19
<211> LENGTH: 21
<212> TYPE: DNA
<213> ORGANISM: artificial
<220> FEATURE:
```

<223> OTHER INFORMATION: PCR primer AF9

<400> SEQUENCE: 19
gaacatgcaa tttggcctgg g                                    21

<210> SEQ ID NO 20
<211> LENGTH: 21
<212> TYPE: DNA
<213> ORGANISM: artificial
<220> FEATURE:
<223> OTHER INFORMATION: PCR primer AR9

<400> SEQUENCE: 20
catcaagata gagcacatgc c                                    21

<210> SEQ ID NO 21
<211> LENGTH: 21
<212> TYPE: DNA
<213> ORGANISM: artificial
<220> FEATURE:
<223> OTHER INFORMATION: PCR primer AF10

<400> SEQUENCE: 21
ggcatgtgct ctatcttgat g                                    21

<210> SEQ ID NO 22
<211> LENGTH: 23
<212> TYPE: DNA
<213> ORGANISM: artificial
<220> FEATURE:
<223> OTHER INFORMATION: PCR primer AR10

<400> SEQUENCE: 22
gctacctctc tatctatagg agc                                  23

<210> SEQ ID NO 23
<211> LENGTH: 20
<212> TYPE: DNA
<213> ORGANISM: artificial
<220> FEATURE:
<223> OTHER INFORMATION: PCR primer AF11

<400> SEQUENCE: 23
agcctctgct ctgtagctgg                                      20

<210> SEQ ID NO 24
<211> LENGTH: 20
<212> TYPE: DNA
<213> ORGANISM: artificial
<220> FEATURE:
<223> OTHER INFORMATION: PCR primer AF12

<400> SEQUENCE: 24
tcttgttccc agcccaaagg                                      20

<210> SEQ ID NO 25
<211> LENGTH: 20
<212> TYPE: DNA
<213> ORGANISM: artificial
<220> FEATURE:
<223> OTHER INFORMATION: PCR primer AR12

<400> SEQUENCE: 25
cctttgggct gggaacaaga                                      20

<210> SEQ ID NO 26

-continued

```
<211> LENGTH: 21
<212> TYPE: DNA
<213> ORGANISM: artificial
<220> FEATURE:
<223> OTHER INFORMATION: PCR primer AR12

<400> SEQUENCE: 26
atcaacctga gagcatccga g                                              21

<210> SEQ ID NO 27
<211> LENGTH: 21
<212> TYPE: DNA
<213> ORGANISM: artificial
<220> FEATURE:
<223> OTHER INFORMATION: PCR primer AF13

<400> SEQUENCE: 27
ctcggatgct ctcaggttga t                                              21

<210> SEQ ID NO 28
<211> LENGTH: 20
<212> TYPE: DNA
<213> ORGANISM: artificial
<220> FEATURE:
<223> OTHER INFORMATION: PCR primer AR13

<400> SEQUENCE: 28
gccattccac aagccccttc                                                20

<210> SEQ ID NO 29
<211> LENGTH: 20
<212> TYPE: DNA
<213> ORGANISM: artificial
<220> FEATURE:
<223> OTHER INFORMATION: PCR primer AF14

<400> SEQUENCE: 29 gaagggctt gaggaatggc                                                 20

<210> SEQ ID NO 30
<211> LENGTH: 20
<212> TYPE: DNA
<213> ORGANISM: artificial
<220> FEATURE:
<223> OTHER INFORMATION: PCR primer AR14

<400> SEQUENCE: 30
aggggtagag atagtcccag                                                20

<210> SEQ ID NO 31
<211> LENGTH: 20
<212> TYPE: DNA
<213> ORGANISM: artificial
<220> FEATURE:
<223> OTHER INFORMATION: PCR primer AF15

<400> SEQUENCE: 31
ctgggactat ctctaccccct                                               20

<210> SEQ ID NO 32
<211> LENGTH: 21
<212> TYPE: DNA
<213> ORGANISM: artificial
<220> FEATURE:
<223> OTHER INFORMATION: PCR primer AR15

<400> SEQUENCE: 32
```

```
gttagggctt gtgtccccat c                                            21

<210> SEQ ID NO 33
<211> LENGTH: 21
<212> TYPE: DNA
<213> ORGANISM: artificial
<220> FEATURE:
<223> OTHER INFORMATION: PCR primer AF16

<400> SEQUENCE: 33
gatggggaca caagccctaa c                                            21

<210> SEQ ID NO 34
<211> LENGTH: 20
<212> TYPE: DNA
<213> ORGANISM: artificial
<220> FEATURE:
<223> OTHER INFORMATION: PCR primer AR16

<400> SEQUENCE: 34
gaggattgga gctgtagggc                                              20

<210> SEQ ID NO 35
<211> LENGTH: 20
<212> TYPE: DNA
<213> ORGANISM: artificial
<220> FEATURE:
<223> OTHER INFORMATION: PCR primer AF17

<400> SEQUENCE: 35
gccctacagc tccaatcctc                                              20

<210> SEQ ID NO 36
<211> LENGTH: 20
<212> TYPE: DNA
<213> ORGANISM: artificial
<220> FEATURE:
<223> OTHER INFORMATION: PCR primer AR17

<400> SEQUENCE: 36
cacctgctga cagtcaccag                                              20

<210> SEQ ID NO 37
<211> LENGTH: 20
<212> TYPE: DNA
<213> ORGANISM: artificial
<220> FEATURE:
<223> OTHER INFORMATION: PCR primer AF18

<400> SEQUENCE: 37
gcaagtggtc ccgcagtaag                                              20

<210> SEQ ID NO 38
<211> LENGTH: 20
<212> TYPE: DNA
<213> ORGANISM: artificial
<220> FEATURE:
<223> OTHER INFORMATION: PCR primer AR18

<400> SEQUENCE: 38
cagtcccatg tggtaggtac                                              20

<210> SEQ ID NO 39
<211> LENGTH: 20
<212> TYPE: DNA
<213> ORGANISM: artificial
<220> FEATURE:
```

```
<223> OTHER INFORMATION: PCR primer AR19

<400> SEQUENCE: 39
gtacctacca catgggactg                                            20

<210> SEQ ID NO 40
<211> LENGTH: 21
<212> TYPE: DNA
<213> ORGANISM: artificial
<220> FEATURE:
<223> OTHER INFORMATION: PCR primer AR19

<400> SEQUENCE: 40
catgtgtaca tgggctgcct g                                          21

<210> SEQ ID NO 41
<211> LENGTH: 21
<212> TYPE: DNA
<213> ORGANISM: artificial
<220> FEATURE:
<223> OTHER INFORMATION: PCR primer STATF1

<400> SEQUENCE: 41
gagaagttgg cggagattat c                                          21

<210> SEQ ID NO 42
<211> LENGTH: 20
<212> TYPE: DNA
<213> ORGANISM: artificial
<220> FEATURE:
<223> OTHER INFORMATION: PCR primer STATR1

<400> SEQUENCE: 42
ccgtgtgtcc tcatcacctg                                            20

<210> SEQ ID NO 43
<211> LENGTH: 20
<212> TYPE: DNA
<213> ORGANISM: artificial
<220> FEATURE:
<223> OTHER INFORMATION: PCR primer STAT14

<400> SEQUENCE: 43
gaggagatgc tggctgaggt                                            20

<210> SEQ ID NO 44
<211> LENGTH: 20
<212> TYPE: DNA
<213> ORGANISM: artificial
<220> FEATURE:
<223> OTHER INFORMATION: PCR primer STAT13

<400> SEQUENCE: 44
ttcaggggac aggactctgg                                            20
```